United States Patent
Hoey

(10) Patent No.: US 9,161,801 B2
(45) Date of Patent: Oct. 20, 2015

(54) MEDICAL SYSTEM AND METHOD OF USE

(75) Inventor: Michael Hoey, Shoreview, MN (US)

(73) Assignee: Tsunami MedTech, LLC, Menlo Park, CA (US)

( * ) Notice: Subject to any disclaimer, the term of this patent is extended or adjusted under 35 U.S.C. 154(b) by 205 days.

(21) Appl. No.: 12/982,573

(22) Filed: Dec. 30, 2010

(65) Prior Publication Data

US 2011/0160648 A1   Jun. 30, 2011

Related U.S. Application Data

(60) Provisional application No. 61/291,315, filed on Dec. 30, 2009.

(51) Int. Cl.
*A61B 18/04* (2006.01)
*A61M 25/06* (2006.01)
(Continued)

(52) U.S. Cl.
CPC .............. *A61B 18/04* (2013.01); *A61M 25/007* (2013.01); *A61M 25/0068* (2013.01); *A61M 25/0082* (2013.01); *A61M 25/0084* (2013.01); *A61M 25/065* (2013.01); *A61M 25/10* (2013.01); *A61M 25/1002* (2013.01); *A61M 25/1011* (2013.01); *A61B 18/1815* (2013.01); *A61B 2018/00011* (2013.01); *A61B 2018/0063* (2013.01); *A61B 2018/00577* (2013.01); *A61B 2018/00589* (2013.01); *A61B 2018/00619* (2013.01); *A61B 2018/048* (2013.01); *A61B 2018/1807* (2013.01); *A61B 2018/1861* (2013.01); *A61M 25/003* (2013.01); *A61M 25/0069* (2013.01); *A61M 25/0074* (2013.01); *A61M 25/0147* (2013.01); *A61M 2025/0002* (2013.01); *A61M 2025/0037* (2013.01); *A61M 2025/0039* (2013.01); *A61M 2025/0057* (2013.01); *A61M 2025/0073* (2013.01); *A61M 2025/0085* (2013.01);
(Continued)

(58) Field of Classification Search
USPC ................... 604/26; 606/27, 28; 607/96, 105
See application file for complete search history.

(56) References Cited

U.S. PATENT DOCUMENTS

| 408,899 A | 8/1889 | Bioch et al. |
| 697,181 A | 4/1902 | Smith |

(Continued)

FOREIGN PATENT DOCUMENTS

| WO | WO 00/11927 | 3/2000 |
| WO | WO 00/29055 | 5/2000 |

(Continued)

OTHER PUBLICATIONS

Coda, et al., "Effects of pulmonary reventilation on gas exchange after cryolytic disobstruction of endobronchial tumors" *Minerva Medical*, vol. 72, pp. 1627-1631, Jun. 1981 (with English translation).

(Continued)

*Primary Examiner* — Kevin C Sirmons
*Assistant Examiner* — William Carpenter
(74) *Attorney, Agent, or Firm* — Levine Bagade Han LLP

(57) ABSTRACT

A system and method for tissue thermotherapy including a source for generating a vapor phase media for treating a space in a human body, such as and intraluminal or intracavity space. The system further includes a filtering member for allowing a recirculation of flowable media about an interface with tissue, wherein the filtering member prevent ablation detritus from interfering with media outflows from the working end.

34 Claims, 31 Drawing Sheets

(51) Int. Cl.
*A61M 25/10* (2013.01)
*A61B 18/18* (2006.01)
*A61B 18/00* (2006.01)
*A61M 25/00* (2006.01)
*A61M 25/01* (2006.01)

(52) U.S. Cl.
CPC .............. *A61M2025/0087* (2013.01); *A61M 2025/1047* (2013.01); *A61M 2025/1086* (2013.01); *A61M 2210/105* (2013.01); *A61M 2210/1042* (2013.01)

(56) References Cited

U.S. PATENT DOCUMENTS

| | | | |
|---|---|---|---|
| 1,719,750 A | 9/1927 | Bridge et al. | |
| 3,818,913 A | 6/1974 | Wallach | |
| 3,880,168 A | 4/1975 | Berman | |
| 3,930,505 A | 1/1976 | Wallach | |
| 4,024,866 A | 5/1977 | Wallach | |
| 4,083,077 A | 4/1978 | Knight et al. | |
| 4,447,227 A * | 5/1984 | Kotsanis | 604/95.03 |
| 4,672,962 A | 6/1987 | Hershenson | |
| 4,682,596 A | 7/1987 | Bales et al. | |
| 4,748,979 A | 6/1988 | Hershenson | |
| 4,773,410 A | 9/1988 | Blackmer et al. | |
| 4,793,352 A | 12/1988 | Eichenlaub | |
| 4,872,920 A | 10/1989 | Flynn et al. | |
| 4,898,574 A | 2/1990 | Uchiyama et al. | |
| 4,915,113 A | 4/1990 | Holman | |
| 4,950,266 A | 8/1990 | Sinofsky | |
| 4,985,027 A | 1/1991 | Dressel | |
| 5,006,119 A | 4/1991 | Acker et al. | |
| 5,011,566 A | 4/1991 | Hoffman | |
| 5,078,736 A | 1/1992 | Behl | |
| 5,084,043 A | 1/1992 | Hertzmann et al. | |
| 5,102,410 A | 4/1992 | Dressel | |
| 5,112,328 A | 5/1992 | Taboada et al. | |
| 5,122,138 A | 6/1992 | Manwaring | |
| 5,158,536 A | 10/1992 | Sekins et al. | |
| 5,162,374 A | 11/1992 | Mulieri et al. | |
| 5,190,539 A | 3/1993 | Fletcher et al. | |
| 5,217,459 A | 6/1993 | Kamerling | |
| 5,217,465 A | 6/1993 | Steppe | |
| 5,263,951 A | 11/1993 | Spears et al. | |
| 5,277,696 A | 1/1994 | Hagen | |
| 5,298,298 A | 3/1994 | Hoffman | |
| 5,306,274 A * | 4/1994 | Long | 606/28 |
| 5,318,014 A | 6/1994 | Carter | |
| 5,331,947 A | 7/1994 | Shturman | |
| 5,334,190 A | 8/1994 | Seiler | |
| 5,344,397 A | 9/1994 | Heaven et al. | |
| 5,348,551 A | 9/1994 | Spears et al. | |
| 5,352,512 A | 10/1994 | Hoffman | |
| 5,417,686 A | 5/1995 | Peterson et al. | |
| 5,424,620 A | 6/1995 | Cheon et al. | |
| 5,433,708 A | 7/1995 | Nichols et al. | |
| 5,433,739 A | 7/1995 | Sluijter | |
| 5,462,521 A | 10/1995 | Brucker et al. | |
| 5,500,012 A | 3/1996 | Brucker et al. | |
| 5,503,638 A | 4/1996 | Cooper et al. | |
| 5,524,620 A | 6/1996 | Rosenschein | |
| 5,529,076 A | 6/1996 | Schachar | |
| 5,542,928 A | 8/1996 | Evans et al. | |
| 5,549,628 A | 8/1996 | Cooper et al. | |
| 5,554,172 A | 9/1996 | Horner et al. | |
| 5,562,608 A | 10/1996 | Sekins et al. | |
| 5,575,803 A | 11/1996 | Cooper et al. | |
| 5,584,872 A | 12/1996 | LaFontaine et al. | |
| 5,591,157 A | 1/1997 | Hennings et al. | |
| 5,591,162 A | 1/1997 | Fletcher et al. | |
| 5,616,120 A | 4/1997 | Andrew et al. | |
| 5,620,440 A | 4/1997 | Heckele et al. | |
| 5,662,671 A * | 9/1997 | Barbut et al. | 606/170 |
| 5,669,907 A | 9/1997 | Platt, Jr. et al. | |
| 5,681,282 A | 10/1997 | Eggers et al. | |
| 5,683,366 A | 11/1997 | Eggers et al. | |
| 5,695,507 A | 12/1997 | Auth et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,700,262 A | 12/1997 | Acosta et al. | |
| 5,707,352 A | 1/1998 | Sekins et al. | |
| 5,735,811 A | 4/1998 | Brisken | |
| 5,741,247 A | 4/1998 | Rizoiu et al. | |
| 5,741,248 A | 4/1998 | Stern et al. | |
| 5,752,965 A | 5/1998 | Francis et al. | |
| 5,755,753 A | 5/1998 | Knowlton | |
| 5,782,914 A | 7/1998 | Schankereli | |
| 5,785,521 A | 7/1998 | Rizoiu et al. | |
| 5,800,482 A | 9/1998 | Pomeranz et al. | |
| 5,810,764 A | 9/1998 | Eggers et al. | |
| 5,824,703 A | 10/1998 | Clark, Jr. | |
| 5,827,268 A | 10/1998 | Laufer | |
| 5,836,896 A | 11/1998 | Rosenschein | |
| 5,843,019 A | 12/1998 | Eggers et al. | |
| 5,843,073 A | 12/1998 | Sinofsky | |
| 5,871,469 A | 2/1999 | Eggers et al. | |
| 5,879,329 A | 3/1999 | Ginsburg | |
| 5,885,243 A | 3/1999 | Capetan et al. | |
| 5,888,198 A | 3/1999 | Eggers et al. | |
| 5,891,095 A | 4/1999 | Eggers et al. | |
| 5,891,134 A | 4/1999 | Goble et al. | |
| 5,911,734 A * | 6/1999 | Tsugita et al. | 606/200 |
| 5,913,856 A | 6/1999 | Chia et al. | |
| 5,938,660 A * | 8/1999 | Swartz et al. | 606/45 |
| 5,944,686 A | 8/1999 | Patterson et al. | |
| 5,944,715 A | 8/1999 | Goble et al. | |
| 5,957,919 A | 9/1999 | Laufer | |
| 5,964,752 A | 10/1999 | Stone | |
| 5,968,037 A | 10/1999 | Rizoiu | |
| 5,980,504 A | 11/1999 | Sharkey et al. | |
| 5,986,662 A | 11/1999 | Argiro et al. | |
| 5,989,212 A | 11/1999 | Sussman et al. | |
| 5,989,238 A | 11/1999 | Ginsburg | |
| 5,989,249 A | 11/1999 | Kirwin | |
| 5,989,445 A | 11/1999 | Wise et al. | |
| 5,997,499 A | 12/1999 | Sussman et al. | |
| 6,024,095 A | 2/2000 | Stanley, III | |
| 6,024,733 A | 2/2000 | Eggers et al. | |
| 6,027,501 A | 2/2000 | Goble et al. | |
| 6,032,077 A | 2/2000 | Pomeranz | |
| 6,032,674 A | 3/2000 | Eggers et al. | |
| 6,047,700 A | 4/2000 | Eggers et al. | |
| 6,053,909 A | 4/2000 | Shadduck | |
| 6,056,746 A | 5/2000 | Goble et al. | |
| 6,059,011 A | 5/2000 | Giolo | |
| 6,063,079 A | 5/2000 | Hovda et al. | |
| 6,063,081 A | 5/2000 | Mulier et al. | |
| 6,066,134 A | 5/2000 | Eggers et al. | |
| 6,066,139 A | 5/2000 | Ryan et al. | |
| 6,074,358 A | 6/2000 | Andrew et al. | |
| 6,080,128 A | 6/2000 | Sussman et al. | |
| 6,080,151 A | 6/2000 | Swartz et al. | |
| 6,083,255 A | 7/2000 | Laufer et al. | |
| 6,095,149 A | 8/2000 | Sharkey et al. | |
| 6,099,251 A | 8/2000 | LaFleur | |
| 6,102,046 A | 8/2000 | Weinstein et al. | |
| 6,102,885 A | 8/2000 | Bass | |
| 6,106,516 A | 8/2000 | Bmassengill | |
| 6,110,162 A | 8/2000 | Sussman et al. | |
| 6,113,722 A | 9/2000 | Hoffman et al. | |
| 6,126,682 A | 10/2000 | Sharkey et al. | |
| 6,130,671 A | 10/2000 | Argiro | |
| 6,139,571 A | 10/2000 | Fuller et al. | |
| 6,149,620 A | 11/2000 | Baker et al. | |
| 6,156,036 A | 12/2000 | Sussman et al. | |
| 6,159,194 A | 12/2000 | Eggers et al. | |
| 6,162,232 A | 12/2000 | Shadduck | |
| 6,168,594 B1 | 1/2001 | LaFontaine et al. | |
| 6,174,308 B1 | 1/2001 | Goble et al. | |
| 6,179,805 B1 | 1/2001 | Sussman et al. | |
| 6,190,381 B1 | 2/2001 | Olsen et al. | |

(56) References Cited

U.S. PATENT DOCUMENTS

| | | |
|---|---|---|
| 6,194,066 B1 | 2/2001 | Hoffman |
| 6,196,989 B1 | 3/2001 | Padget et al. |
| 6,200,333 B1 | 3/2001 | Laufer |
| 6,206,848 B1 | 3/2001 | Sussman et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,654 B1 | 7/2001 | Swartz et al. |
| 6,277,112 B1 | 8/2001 | Underwood et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,287,274 B1 | 9/2001 | Sussman et al. |
| 6,290,715 B1 | 9/2001 | Sharkey et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,312,408 B1 | 11/2001 | Eggers et al. |
| 6,312,474 B1 | 11/2001 | Francis et al. |
| 6,315,755 B1 | 11/2001 | Sussman |
| 6,319,222 B1 | 11/2001 | Andrew et al. |
| 6,327,505 B1 | 12/2001 | Medhkour et al. |
| 6,331,171 B1 | 12/2001 | Cohen |
| 6,355,032 B1 | 3/2002 | Hovda et al. |
| 6,375,635 B1 | 4/2002 | Moutafis et al. |
| 6,379,350 B1 | 4/2002 | Sharkey et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,723 B1 | 6/2002 | Edwards |
| 6,416,508 B1 | 7/2002 | Eggers et al. |
| 6,458,231 B1 | 10/2002 | Wapner et al. |
| 6,461,350 B1 | 10/2002 | Underwood et al. |
| 6,464,694 B1 | 10/2002 | Massengill |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,482,201 B1 | 11/2002 | Olsen et al. |
| 6,482,202 B1 | 11/2002 | Goble et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,517,568 B1 | 2/2003 | Sharkey et al. |
| 6,522,930 B1 | 2/2003 | Schaer et al. |
| 6,527,761 B1 | 3/2003 | Soltesz et al. |
| 6,527,766 B1 | 3/2003 | Bair |
| 6,540,741 B1 | 4/2003 | Underwood et al. |
| 6,544,211 B1 | 4/2003 | Andrew et al. |
| 6,544,248 B1 | 4/2003 | Bass |
| 6,547,810 B1 | 4/2003 | Sharkey et al. |
| 6,558,379 B1 | 5/2003 | Batchelor et al. |
| 6,569,146 B1 * | 5/2003 | Werner et al. ................ 604/509 |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,204 B1 | 7/2003 | Sussman et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,605,087 B2 | 8/2003 | Swartz et al. |
| 6,610,043 B1 | 8/2003 | Ingenito |
| 6,620,130 B1 | 9/2003 | Ginsburg |
| 6,620,155 B1 | 9/2003 | Underwood et al. |
| 6,623,444 B2 | 9/2003 | Babaev |
| 6,632,193 B1 | 10/2003 | Davison et al. |
| 6,632,220 B1 | 10/2003 | Eggers et al. |
| 6,634,363 B1 | 10/2003 | Danek et al. |
| 6,648,847 B2 | 11/2003 | Sussman et al. |
| 6,652,594 B2 | 11/2003 | Francis et al. |
| 6,653,525 B2 | 11/2003 | Ingenito et al. |
| 6,659,106 B1 | 12/2003 | Hovda et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,682,520 B2 | 1/2004 | Ingenito |
| 6,682,543 B2 * | 1/2004 | Barbut et al. ................ 606/159 |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,712,811 B2 | 3/2004 | Underwood et al. |
| 6,712,812 B2 | 3/2004 | Roschak et al. |
| 6,719,738 B2 | 4/2004 | Mehier |
| 6,719,754 B2 | 4/2004 | Underwood et al. |
| 6,723,064 B2 | 4/2004 | Babaev |
| 6,726,684 B1 | 4/2004 | Woloszko et al. |
| 6,726,708 B2 | 4/2004 | Lasheras |
| 6,746,447 B2 | 6/2004 | Davison et al. |
| 6,755,794 B2 | 6/2004 | Soukup |
| 6,758,846 B2 | 7/2004 | Goble et al. |
| 6,763,836 B2 | 7/2004 | Tasto et al. |
| 6,764,487 B2 | 7/2004 | Mulier et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Woloszko et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Wolosko et al. |
| 6,896,675 B2 | 5/2005 | Leung et al. |
| 6,896,690 B1 * | 5/2005 | Lambrecht et al. ........... 606/200 |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Wolosko et al. |
| 7,022,088 B2 | 4/2006 | Keast et al. |
| 7,031,504 B1 | 4/2006 | Argiro et al. |
| 7,083,612 B2 | 8/2006 | Littrup et al. |
| 7,094,249 B1 * | 8/2006 | Broome et al. ............... 606/200 |
| 7,128,748 B2 | 10/2006 | Mooradian et al. |
| 7,136,064 B2 | 11/2006 | Zuiderveld |

(56) References Cited

U.S. PATENT DOCUMENTS

| | | | |
|---|---|---|---|
| 7,144,402 B2 | 12/2006 | Kuester, III | |
| 7,144,588 B2 | 12/2006 | Oray et al. | |
| 7,162,303 B2 | 1/2007 | Levin et al. | |
| 7,192,400 B2 | 3/2007 | Campbell et al. | |
| 7,233,820 B2 | 6/2007 | Gilboa | |
| 7,235,070 B2 | 6/2007 | Vanney | |
| 7,311,708 B2 * | 12/2007 | McClurken | 606/50 |
| 7,335,195 B2 | 2/2008 | Mehier | |
| 7,347,859 B2 | 3/2008 | Garabedian et al. | |
| 7,524,315 B2 * | 4/2009 | Blott et al. | 604/543 |
| 7,549,987 B2 | 6/2009 | Shadduck | |
| 7,585,295 B2 | 9/2009 | Ben-Nun | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,674,259 B2 | 3/2010 | Shadduck | |
| 7,717,948 B2 | 5/2010 | Demarais et al. | |
| 7,756,583 B2 | 7/2010 | Demarais et al. | |
| 7,815,616 B2 * | 10/2010 | Boehringer et al. | 604/313 |
| 7,853,333 B2 | 12/2010 | Demarais | |
| 7,873,417 B2 | 1/2011 | Demarais et al. | |
| 7,892,229 B2 | 2/2011 | Shadduck et al. | |
| 7,937,143 B2 | 5/2011 | Demarais et al. | |
| 7,993,323 B2 | 8/2011 | Barry et al. | |
| 8,016,823 B2 | 9/2011 | Shadduck | |
| 8,131,371 B2 | 3/2012 | Demarals et al. | |
| 8,131,372 B2 | 3/2012 | Levin et al. | |
| 8,145,316 B2 | 3/2012 | Deem et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 8,187,269 B2 | 5/2012 | Shadduck et al. | |
| 8,192,424 B2 | 6/2012 | Woloszko | |
| 8,313,485 B2 | 11/2012 | Shadduck | |
| 8,444,636 B2 | 5/2013 | Shadduck et al. | |
| 8,574,226 B2 | 11/2013 | Shadduck | |
| 8,579,888 B2 | 11/2013 | Hoey et al. | |
| 8,579,892 B2 | 11/2013 | Hoey et al. | |
| 8,579,893 B2 | 11/2013 | Hoey | |
| 2001/0020167 A1 | 9/2001 | Woloszko et al. | |
| 2001/0029370 A1 | 10/2001 | Hodva et al. | |
| 2001/0037106 A1 | 11/2001 | Shadduck | |
| 2002/0049438 A1 | 4/2002 | Sharkey et al. | |
| 2002/0077516 A1 | 6/2002 | Flanigan | |
| 2002/0078956 A1 | 6/2002 | Sharpe et al. | |
| 2002/0082667 A1 | 6/2002 | Shadduck | |
| 2002/0095152 A1 | 7/2002 | Ciarrocca et al. | |
| 2002/0111386 A1 | 8/2002 | Sekins et al. | |
| 2002/0128638 A1 | 9/2002 | Chauvet et al. | |
| 2002/0133147 A1 | 9/2002 | Marchitto et al. | |
| 2002/0151917 A1 * | 10/2002 | Barry | 606/159 |
| 2002/0161326 A1 | 10/2002 | Sussman et al. | |
| 2002/0173815 A1 * | 11/2002 | Hogendijk et al. | 606/194 |
| 2002/0177846 A1 | 11/2002 | Mulier et al. | |
| 2002/0193789 A1 | 12/2002 | Underwood et al. | |
| 2003/0028189 A1 | 2/2003 | Woloszko et al. | |
| 2003/0040742 A1 | 2/2003 | Underwood et al. | |
| 2003/0097126 A1 | 5/2003 | Woloszko et al. | |
| 2003/0097129 A1 * | 5/2003 | Davison et al. | 606/41 |
| 2003/0099279 A1 | 5/2003 | Venkatasubramanian et al. | |
| 2003/0109869 A1 | 6/2003 | Shadduck | |
| 2003/0130655 A1 | 7/2003 | Woloszko et al. | |
| 2003/0130738 A1 | 7/2003 | Hovda et al. | |
| 2003/0144654 A1 | 7/2003 | Hilal | |
| 2003/0158545 A1 | 8/2003 | Hovda et al. | |
| 2003/0163178 A1 | 8/2003 | Davison et al. | |
| 2003/0181922 A1 | 9/2003 | Alferness | |
| 2003/0212394 A1 | 11/2003 | Pearson et al. | |
| 2003/0212395 A1 | 11/2003 | Woloszko et al. | |
| 2003/0225364 A1 | 12/2003 | Kraft et al. | |
| 2004/0024398 A1 | 2/2004 | Hovda et al. | |
| 2004/0024399 A1 | 2/2004 | Sharps et al. | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0049180 A1 | 3/2004 | Sharps et al. | |
| 2004/0054366 A1 | 3/2004 | Davison et al. | |
| 2004/0055606 A1 | 3/2004 | Hendricksen et al. | |
| 2004/0068256 A1 | 4/2004 | Rizoiu et al. | |
| 2004/0068306 A1 | 4/2004 | Shadduck | |
| 2004/0087937 A1 | 5/2004 | Eggers et al. | |
| 2004/0116922 A1 | 6/2004 | Hovda et al. | |
| 2004/0193150 A1 | 9/2004 | Sharkey et al. | |
| 2004/0199226 A1 | 10/2004 | Shadduck | |
| 2004/0230190 A1 | 11/2004 | Dahla et al. | |
| 2004/0254532 A1 | 12/2004 | Mehier | |
| 2005/0004634 A1 | 1/2005 | Ricart et al. | |
| 2005/0010205 A1 | 1/2005 | Hovda et al. | |
| 2005/0070894 A1 * | 3/2005 | McClurken | 606/48 |
| 2005/0119650 A1 | 6/2005 | Sanders et al. | |
| 2005/0166925 A1 | 8/2005 | Wilson et al. | |
| 2005/0171582 A1 | 8/2005 | Matlock | |
| 2005/0187543 A1 | 8/2005 | Underwood et al. | |
| 2005/0215991 A1 | 9/2005 | Altman et al. | |
| 2005/0222485 A1 | 10/2005 | Shaw et al. | |
| 2005/0228423 A1 | 10/2005 | Khashayar et al. | |
| 2005/0228424 A1 | 10/2005 | Khashayar et al. | |
| 2005/0240171 A1 | 10/2005 | Forrest | |
| 2005/0267467 A1 | 12/2005 | Paul et al. | |
| 2005/0267468 A1 * | 12/2005 | Truckai et al. | 606/41 |
| 2005/0283143 A1 | 12/2005 | Rizoiu | |
| 2006/0004400 A1 | 1/2006 | McGurk et al. | |
| 2006/0047291 A1 | 3/2006 | Barry | |
| 2006/0085054 A1 | 4/2006 | Zikorus et al. | |
| 2006/0100619 A1 | 5/2006 | McClurken et al. | |
| 2006/0130830 A1 | 6/2006 | Barry | |
| 2006/0135955 A1 | 6/2006 | Shadduck | |
| 2006/0142783 A1 | 6/2006 | Lewis et al. | |
| 2006/0161233 A1 * | 7/2006 | Barry et al. | 607/113 |
| 2006/0200076 A1 | 9/2006 | Gonzalez et al. | |
| 2006/0206150 A1 | 9/2006 | Demarais et al. | |
| 2006/0224154 A1 | 10/2006 | Shadduck et al. | |
| 2006/0271111 A1 | 11/2006 | Demarais et al. | |
| 2007/0032785 A1 | 2/2007 | Diederich et al. | |
| 2007/0036417 A1 | 2/2007 | Argiro et al. | |
| 2007/0091087 A1 | 4/2007 | Zuiderveld | |
| 2007/0129720 A1 | 6/2007 | Demarais et al. | |
| 2007/0129760 A1 | 6/2007 | Demarais et al. | |
| 2007/0129761 A1 | 6/2007 | Demarais et al. | |
| 2007/0135875 A1 | 6/2007 | Demarais et al. | |
| 2007/0265687 A1 | 11/2007 | Deem et al. | |
| 2008/0033493 A1 | 2/2008 | Deckman et al. | |
| 2008/0097429 A1 * | 4/2008 | McClurken | 606/50 |
| 2008/0103566 A1 | 5/2008 | Mehier | |
| 2008/0110457 A1 | 5/2008 | Barry et al. | |
| 2008/0114297 A1 | 5/2008 | Barry et al. | |
| 2008/0125747 A1 | 5/2008 | Prokop | |
| 2008/0132826 A1 | 6/2008 | Shadduck et al. | |
| 2008/0213331 A1 | 9/2008 | Gelfand et al. | |
| 2008/0255642 A1 | 10/2008 | Zarins et al. | |
| 2009/0030412 A1 * | 1/2009 | Willis et al. | 606/41 |
| 2009/0036948 A1 | 2/2009 | Levin et al. | |
| 2009/0054871 A1 | 2/2009 | Sharkey et al. | |
| 2009/0062873 A1 | 3/2009 | Wu et al. | |
| 2009/0076409 A1 | 3/2009 | Wu et al. | |
| 2009/0105702 A1 | 4/2009 | Shadduck | |
| 2009/0105703 A1 | 4/2009 | Shadduck | |
| 2009/0125009 A1 | 5/2009 | Zikorus et al. | |
| 2009/0149846 A1 * | 6/2009 | Hoey et al. | 606/27 |
| 2009/0216220 A1 | 8/2009 | Hoey et al. | |
| 2009/0306640 A1 | 12/2009 | Glaze et al. | |
| 2009/0312753 A1 | 12/2009 | Shadduck | |
| 2010/0076416 A1 | 3/2010 | Hoey et al. | |
| 2010/0094270 A1 * | 4/2010 | Sharma | 606/27 |
| 2010/0114083 A1 * | 5/2010 | Sharma | 606/27 |
| 2010/0137860 A1 | 6/2010 | Demarais et al. | |
| 2010/0137952 A1 | 6/2010 | Demarais et al. | |
| 2010/0160905 A1 | 6/2010 | Shadduck | |
| 2010/0168731 A1 | 7/2010 | Wu et al. | |
| 2010/0168739 A1 | 7/2010 | Wu et al. | |
| 2010/0174282 A1 | 7/2010 | Demarais et al. | |

(56) References Cited

U.S. PATENT DOCUMENTS

| | | |
|---|---|---|
| 2010/0179528 A1 | 7/2010 | Shadduck et al. |
| 2010/0185189 A1 | 7/2010 | Hoey |
| 2010/0191112 A1 | 7/2010 | Demarais et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0262133 A1 | 10/2010 | Hoey et al. |
| 2010/0268307 A1 | 10/2010 | Demarais et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0208096 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2012/0259271 A1 | 10/2012 | Shadduck et al. |
| 2013/0079772 A1 | 3/2013 | Shadduck |
| 2013/0116683 A1 | 5/2013 | Shadduck et al. |
| 2013/0237978 A1 | 9/2013 | Shadduck et al. |
| 2014/0018890 A1 | 1/2014 | Hoey et al. |
| 2014/0025057 A1 | 1/2014 | Hoey et al. |
| 2014/0031805 A1 | 1/2014 | Shadduck |

FOREIGN PATENT DOCUMENTS

| | | |
|---|---|---|
| WO | WO 02/069821 | 9/2002 |
| WO | WO 03/070302 | 8/2003 |
| WO | WO 03/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," *N Engl J Med*, vol. 348, No. 21, pp. 2059-2073, May 22, 2003.

Homasson, et al., "Bronchoscopic cryotherapy for airway strictures caused by tumors" *Chest*, vol. 90, No. 2, pp. 159-164, Aug. 1986.

Li, K., "Efficient optimal net surface detection for image segmentation—from theory to practice" M.Sc. Thesis, The University of Iowa, 2003.

Marasso, et al., "Cryosurgery in bronchoscopic treatment of tracheobronchial stenosis," *Chest*, vol. 103, No. 2, pp. 472-474, Feb. 1993.

Marasso, et al., "Radiofrequency resection of bronchial tumours in combination with cryotherapy: evaluation of a new technique," *Thorax*, vol. 53, pp. 106-109, 1998.

Mathur et al., "Fiberoptic bronchoscopic cryotherapy in the management of tracheobronchial obstruction," *Chest*, vol. 110, No. 3, pp. 718-723. Sep. 1996.

Morice et al. "Endobrinchial argon plasma coagulation for treatment of hemotysis and neoplastic airway obstruction," *Chest*, vol. 119, No. 3, pp. 781-787, Mar. 2001.

Moulding et al., "Preliminary studies for achieving transcervical oviduct occlusion by hot water or low-pressure stream," *Advances in Planned Parenthood*, vol. 12, No. 2; pp. 79-85, 1977.

Quin, J., "Use of neodymium yttrium aluminum garnet laser in long-term palliation of airway obstruction," *Connecticut Medicine*, vol. 59, No. 7, pp. 407-412, Jul. 1995.

Sutedja, et al., "Bronchoscopic treatment of lung tumors," *Elsevier, Lung Cancer*, 11, pp. 1-17, 1994.

Tschirren et al.; "Intrathoracic airway trees: segmentation and airway morphology analysis from low-dose CT scans;" *IEEE Trans. Med. Imaging*, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," *Science*, vol. 288, pp. 113-116, Apr. 7, 2000, accessed at http://web.mit.edu/thorsen/www/113.pdf.

Xia, Y. et al. "Soft Lithography," *Annu. Rev. Mater. Sci.*, vol. 28, pp. 153-184, 1998, accessed at http://www.bwfoundry.com/xia.pdf.

* cited by examiner

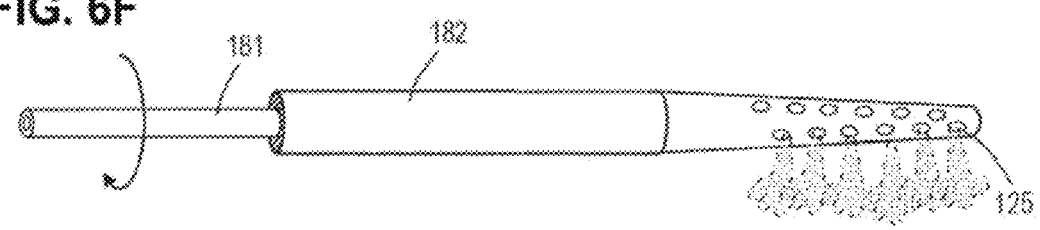
FIG. 6F
FIG. 6G
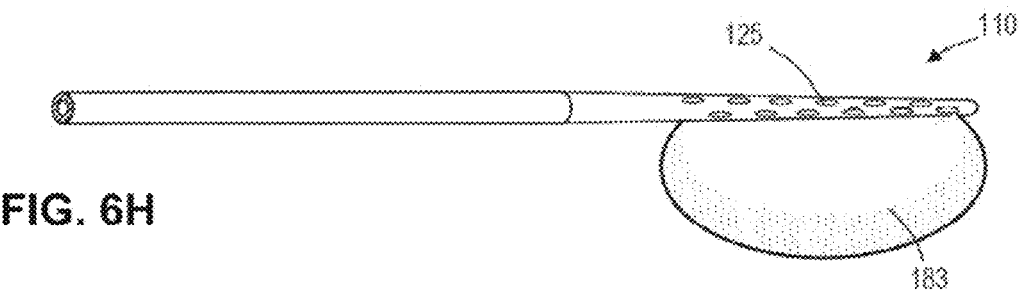
FIG. 6H
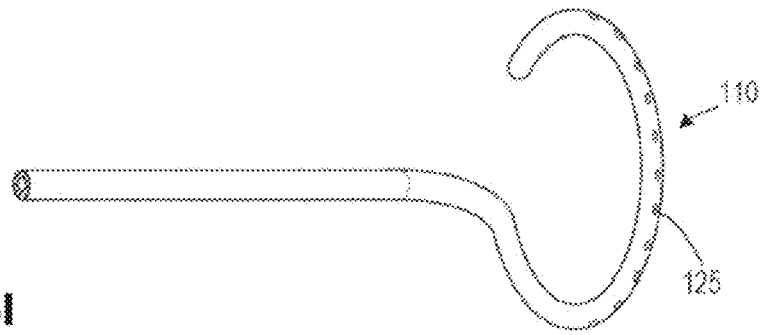
FIG. 6I

MEDICAL SYSTEM AND METHOD OF USE

CROSS-REFERENCE TO RELATED APPLICATIONS

This application claims benefit of U.S. Provisional Application No. 61/291,315 filed on Dec. 30, 2009 and titled MEDICAL SYSTEM AND METHOD OF USE the entirety of which is incorporated herein by reference.

FIELD OF THE INVENTION

This invention relates to medical instruments and systems for applying energy to tissue, and more particularly relates to a system for ablating, sealing, welding, coagulating, shrinking or creating lesions in tissue by means of contacting a targeted region of tissue in a patient with a vapor phase media wherein a subsequent vapor-to-liquid phase change of the media applies thermal energy to the tissue to cause an intended therapeutic effect. Variations of the invention include devices and methods for generating a flow of high quality vapor and monitoring the vapor flow for various parameters with one or more sensors. In yet additional variations, the invention includes devices and methods for modulating parameters of the system in response to the observed parameters.

BACKGROUND OF THE INVENTION

Various types of medical instruments utilizing radiofrequency (Rf) energy, laser energy, microwave energy and the like have been developed for delivering thermal energy to tissue, for example to ablate tissue. While such prior art forms of energy delivery work well for some applications, Rf, laser and microwave energy typically cannot cause highly "controlled" and "localized" thermal effects that are desirable in controlled ablation soft tissue for ablating a controlled depth or for the creation of precise lesions in such tissue. In general, the non-linear or non-uniform characteristics of tissue affect electromagnetic energy distributions in tissue.

What is needed are systems and methods that controllably apply thermal energy in a controlled and localized manner without the lack of control often associated when Rf, laser and microwave energy are applied directly to tissue.

SUMMARY OF THE INVENTION

The present invention is adapted to provide improved methods of controlled thermal energy delivery to localized tissue volumes, for example for ablating, sealing, coagulating or otherwise damaging targeted tissue, for example to ablate a tissue volume interstitially or to ablate the lining of a body cavity. Of particular interest, the method causes thermal effects in targeted tissue without the use of Rf current flow through the patient's body and without the potential of carbonizing tissue. The devices and methods of the present disclosure allow the use of such energy modalities to be used as an adjunct rather than a primary source of treatment.

One variation of the present novel method includes a method of delivering energy into a target tissue of a body region, the method comprising advancing a working end of a device into the body region, expanding a structure from within a working end of the device into the body region, where at least a portion of the thin wall structure is permeable to allow transfer of a medium through the structure to the tissue, and delivering an amount of energy from the structure to treat the target tissue of the body region.

Expanding the structure can include everting the structure. Although the variations described below discuss everting the structure, alternate variations can include inflating, unfolding, unfurling or unrolling the structure. Typically, these different expansion modes relate to the manner in which the structure is located (partially or fully) within the working end of the device. In any case, many variations of the method and device allow for the structure to expand to (or substantially) to the cavity or tissue region being treated. As such, the structure can comprise a thin wall structure or other structure that allows for delivery of the vapor media therethrough. Expansion of the structure can occur using a fluid or gas. Typically the expansion pressure is low, however, alternate variations can include the use of high pressure expansion. In such a variation, the expansion of the structure can be used to perform a therapeutic treatment in conjunction with the energy delivery.

Typically, the energy applied by the vapor media is between 25 W and 150 W. In additional variations, the vapor media can apply a first amount of energy with alternate energy modalities being used to provide additional amounts of energy as required by the particular application or treatment. Such additional energy modalities include RF energy, light energy, radiation, resistive heating, chemical energy and/or microwave energy. In some cases, the treatment ablates the target tissue. In alternate variations, the treatment coagulates or heats the tissue to affect a therapeutic purpose. The additional modalities of energy can be applied from elements that are in the expandable structure or on a surface of the structure.

Turning now to the vapor delivery, as described below, the vapor transfers an amount of energy to the tissue without charring or desiccating the tissue. In certain variations, delivering the amount of energy comprises delivering energy using a vapor media by passing the vapor media through the structure. Accordingly, the expandable structure can include at least one vapor outlet. However, additional variations of the method or device can include structures that include a plurality of permeable portions, where at least a porosity of one of the permeable portion varies such that delivery of the amount of energy is non-uniform about the structure when expanded. In one example, delivering the amount of energy comprises delivering a first amount of energy at a central portion of the structure when expanded and a second amount of energy at a distal or proximal portion, and where the first amount of energy is different than the second amount of energy.

In those variations that employ additional energy delivery means, a second amount of energy can be delivered from a portion of the structure. For example, electrodes, antennas, or emitters, can be positioned on or within the structure.

The structures included within the scope of the methods and devices described herein can include any shape as required by the particular application. Such shapes include, but are not limited to round, non-round, flattened, cylindrical, spiraling, pear-shaped, triangular, rectangular, square, oblong, oblate, elliptical, banana-shaped, donut-shaped, pancake-shaped or a plurality or combination of such shapes when expanded. The shape can even be selected to conform to a shape of a cavity within the body (e.g., a passage of the esophagus, a chamber of the heart, a portion of the GI tract, the stomach, blood vessel, lung, uterus, cervical canal, fallopian tube, sinus, airway, gall bladder, pancreas, colon, intestine, respiratory tract, etc.)

In additional variations, the devices and methods described herein can include one or more additional expanding members. Such additional expanding members can be positioned at a working end of the device. The second expandable member can include a surface for engaging a non-targeted region to limit the energy from transferring to the non-targeted region. The second expandable member can be insulated to protect the non-targeted region. Alternatively, or in combination, the second expandable member can be expanded using a cooling fluid where the expandable member conducts cooling to the non-targeted region. Clearly, any number of additional expandable members can be used. In one variation, an expandable member can be used to seal an opening of the cavity.

In certain variations, the device or method includes the use of one or more vacuum passages so that upon monitoring a cavity pressure within the cavity, to relieve pressure when the cavity pressure reaches a pre-determined value.

In another variation, a device according to the present disclosure can include an elongated device having an axis and a working end, a vapor source communicating with at least one vapor outlet in the working end, the vapor source providing a condensable vapor through the vapor outlet to contact the targeted tissue region, such that when the condensable vapor contacts the targeted tissue region, an amount of energy transfers from the condensable vapor to the targeted tissue region, and at least one expandable member is carried by the working end, the expandable member having a surface for engaging a non-targeted tissue region to limit contact and energy transfer between the condensable vapor and the non-targeted tissue region.

In one variation a first and second expandable members are disposed axially proximal of the at least one vapor outlet. This allows treatment distal to the expandable members. In another variation, at least one vapor outlet is intermediate the first and second expandable members. Therefore, the treatment occurs between the expandable members. In yet another variation, at least one expandable member is radially positioned relative to at least one vapor outlet to radially limit the condensable vapor from engaging the non-targeted region.

In additional variation of the methods and devices, the expandable member(s) is fluidly coupled to a fluid source for expanding the expandable member. The fluid source can optionally comprise a cooling fluid that allows the expandable member to cool tissue via conduction through the surface of the expandable member.

In another variation of a method under the principles of the present invention, the method includes selectively treating a target region of tissue and preserving a non-target region of tissue within a body region. For example, the method can include introducing a working end of an axially-extending vapor delivery tool into cavity or lumen, the working end comprising at least one vapor outlet being fluidly coupleable to a vapor source having a supply of vapor, expanding at least one expandable member carried by the working end to engage the non-target region of tissue, and delivering the vapor through the vapor outlet to the target region tissue to cause energy exchange between the vapor and the target region tissue such that vapor contact between the non-target region of tissue is minimized or prevented by the at least one expanding member.

The methods described herein can also include a variation of treating esophageal tissue of a patient's body. In such a case, any of the variations of the devices described herein can be used. In any case, an example of the method includes introducing an elongate vapor delivery tool into an esophageal passage, the vapor delivery tool being coupleable to a supply of vapor, delivering the vapor through the delivery tool into the passage, and controlling energy application to a surface of the passage by controlling interaction between the vapor and the surface of the passage. In an additional variation, the elongate vapor delivery tool includes a vapor lumen and a vacuum lumen, where the vapor lumen and vacuum lumen are in fluid communication, where controlling interaction between the vapor and the surface of the passage comprises modulating delivery of a vapor inflow through the vapor lumen and modulating vacuum outflow through the vacuum lumen. The method can further include applying a cooling media to the surface of the passage to limit diffusion of heat in the surface.

Methods of the present disclosure also include methods of reducing diabetic conditions. For example, the method can include treating a patient to reduce diabetic conditions by inserting a vapor delivery device to an digestive passage, where the vapor delivery device is coupleable to a source of vapor, delivering the vapor to a wall of the digestive tract to transfer energy from the vapor to the wall in a sufficient amount to alter a function of the digestive tract, and controlling interaction between the vapor and the wall to cause controlled ablation at the a treatment area. The treatment can be applied in an organ selected from the group consisting of the stomach, the small intestines, the large intestines, and the duodenum. In some variations, controlling interaction between the vapor and the wall causes a thin ablation layer on a surface of the wall.

The present disclosure also includes medical systems for applying thermal energy to tissue, where the system comprises an elongated probe with an axis having an interior flow channel extending to at least one outlet in a probe working end; a source of vapor media configured to provide a vapor flow through at least a portion of the interior flow channel, wherein the vapor has a minimum temperature; and at least one sensor in the flow channel for providing a signal of at least one flow parameter selected from the group one of (i) existence of a flow of the vapor media, (ii) quantification of a flow rate of the vapor media, and (iii) quality of the flow of the vapor media. The medical system can include variations where the minimum temperature varies from at least 80° C., 100° C. 120° C., 140° C. and 160° C. However, other temperature ranges can be included depending upon the desired application.

Sensors included in the above system include temperature sensor, an impedance sensor, a pressure sensor as well as an optical sensor.

The source of vapor media can include a pressurized source of a liquid media and an energy source for phase conversion of the liquid media to a vapor media. In addition, the medical system can further include a controller capable of modulating a vapor parameter in response to a signal of a flow parameter; the vapor parameter selected from the group of (i) flow rate of pressurized source of liquid media, (ii) inflow pressure of the pressurized source of liquid media, (iii) temperature of the liquid media, (iv) energy applied from the energy source to the liquid media, (v) flow rate of vapor media in the flow channel, (vi) pressure of the vapor media in the flow channel, (vi) temperature of the vapor media, and (vii) quality of vapor media.

In another variation, a novel medical system for applying thermal energy to tissue comprises an elongated probe with an axis having an interior flow channel extending to at least one outlet in a probe working end, wherein a wall of the flow channel includes an insulative portion having a thermal conductivity of less than a maximum thermal conductivity; and a source of vapor media configured to provide a vapor flow through at least a portion of the interior flow channel, wherein the vapor has a minimum temperature.

Variations of such systems include systems where the maximum thermal conductivity ranges from 0.05 W/mK, 0.01 W/mK and 0.005 W/mK.

Methods are disclosed herein for thermally treating tissue by providing a probe body having a flow channel extending therein to an outlet in a working end, introducing a flow of a liquid media through the flow channel and applying energy to the tissue by inductively heating a portion of the probe sufficient to vaporize the flowing media within the flow channel causing pressurized ejection of the media from the outlet to the tissue.

The methods can include applying energy between 10 and 10,000 Joules to the tissue from the media. The rate at which the media flows can be controlled as well.

In another variation, the methods described herein include inductively heating the portion of the probe by applying an electromagnetic energy source to a coil surrounding the flow channel. The electromagnetic energy can also inductively heat a wall portion of the flow channel.

Another variation of the method includes providing a flow permeable structure within the flow channel. Optionally, the coil described herein can heat the flow permeable structure to transfer energy to the flow media. Some examples of a flow permeable structure include woven filaments, braided filaments, knit filaments, metal wool, a microchannel structure, a porous structure, a honeycomb structure and an open cell structure. However, any structure that is permeable to flow can be included.

The electromagnetic energy source can include an energy source ranging from a 10 Watt source to a 500 Watt source.

Medical systems for treating tissue are also described herein. Such systems can include a probe body having a flow channel extending therein to an outlet in a working end, a coil about at least a portion or the flow channel, and an electromagnetic energy source coupled to the coil, where the electromagnetic energy source induces current in the coil causing energy delivery to a flowable media in the flow channel. The systems can include a source of flowable media coupled to the flow channel. The electromagnetic energy source can be capable of applying energy to the flowable media sufficient to cause a liquid-to-vapor phase change in at least a portion of the flowable media as described in detail herein. In addition the probe can include a sensor selected from a temperature sensor, an impedance sensor, a capacitance sensor and a pressure sensor. In some variations the probe is coupled to an aspiration source.

The medical system can also include a controller capable of modulating at least one operational parameter of the source of flowable media in response to a signal from a sensor. For example, the controller can be capable of modulating a flow of the flowable media. In another variation, the controller is capable of modulating a flow of the flowable media to apply between 100 and 10,000 Joules to the tissue.

The systems described herein can also include a metal portion in the flow channel for contacting the flowable media. The metal portion can be a flow permeable structure and can optionally comprise a microchannel structure. In additional variations, the flow permeable structure can include woven filaments, braided filaments, knit filaments, metal wool, a porous structure, a honeycomb structure, an open cell structure or a combination thereof.

In another variation, the methods described herein can include positioning a probe in an interface with a targeted tissue, and causing a vapor media from to be ejected from the probe into the interface with tissue wherein the media delivers energy ranging from 5 joules to 100,000 joules to cause a therapeutic effect, wherein the vapor media is converted from a liquid media within the probe by inductive heating means.

Methods described herein also include methods of treating tissue by providing medical system including a heat applicator portion for positioning in an interface with targeted tissue, and converting a liquid media into a vapor media within an elongated portion of the medical system having a flow channel communicating with a flow outlet in the heat applicator portion, and contacting the vapor media with the targeted tissue to thereby deliver energy ranging from 5 joules to 100,000 joules to cause a therapeutic effect.

As discussed herein, the methods can include converting the liquid into a vapor media using an inductive heating means. In an alternate variation, a resistive heating means can be combined with the inductive heating means or can replace the inductive heating means.

The instrument and method of the invention can cause an energy-tissue interaction that is imagable with intra-operative ultrasound or MRI.

The instrument and method of the invention cause thermal effects in tissue that do not rely applying an electrical field across the tissue to be treated.

Additional advantages of the invention will be apparent from the following description, the accompanying drawings and the appended claims.

All patents, patent applications and publications mentioned in this specification are herein incorporated by reference to the same extent as if each individual publication or patent application was specifically and individually indicated to be incorporated by reference.

In addition, it is intended that combinations of aspects of the systems and methods described herein as well as the various embodiments themselves, where possible, are within the scope of this disclosure.

This application is related to the following U.S Non-provisional and Provisional applications: Application No. 61/126,647 Filed on May 6, 2008 MEDICAL SYSTEM AND METHOD OF USE; Application No. 61/126,651 Filed on May 6, 2008 MEDICAL SYSTEM AND METHOD OF USE; U.S. Application No. 61/126,612 Filed on May 6, 2008 MEDICAL SYSTEM AND METHOD OF USE; Application No. 61/126,636 Filed on May 6, 2008 MEDICAL SYSTEM AND METHOD OF USE; Application No. 61/130,345 Filed on May 31, 2008 MEDICAL SYSTEM AND METHOD OF USE; Application No. 61/066,396 Filed on Feb. 20, 2008 TISSUE ABLATION SYSTEM AND METHOD OF USE; Application No. 61/123,416 Filed on Apr. 8, 2008 MEDICAL SYSTEM AND METHOD OF USE; Application No. 61/068,049 Filed on Mar. 4, 2008 MEDICAL SYSTEM AND METHOD OF USE; Application No. 61/123,384 Filed on Apr. 8, 2008 MEDICAL SYSTEM AND METHOD OF USE; Application No. 61/068,130 Filed on Mar. 4, 2008 MEDICAL SYSTEM AND METHOD OF USE; Application No. 61/123,417 Filed on Apr. 8, 2008 MEDICAL SYSTEM AND METHOD OF USE; Application No. 61/123,412 Filed on Apr. 8, 2008 MEDICAL SYSTEM AND METHOD OF USE; Application No. 61/126,830 Filed on May 7, 2008 MEDICAL SYSTEM AND METHOD OF USE; and Application No. 61/126,620 Filed on May 6, 2008 MEDICAL SYSTEM AND METHOD OF USE.

The systems and methods described herein are also related to U.S. patent application Ser. No. 10/681,625 filed Oct. 7, 2003 titled "Medical Instruments and Techniques for Thermally-Mediated Therapies"; Ser. No. 11/158,930 filed Jun. 22, 2005 titled "Medical Instruments and Techniques for Treating Pulmonary Disorders"; Ser. No. 11/244,329 filed Oct. 5, 2005 titled "Medical Instruments and Methods of Use" and Ser. No. 11/329,381 filed Jan. 10, 2006 titled "Medical Instrument and Method of Use".

All of the above applications are incorporated herein by this reference and made a part of this specification, together with the specifications of all other commonly-invented applications cited in the above applications.

BRIEF DESCRIPTION OF THE DRAWINGS

FIG. 6F is schematic view of a working end with a rotating element for directing vapor flows.

FIG. 6G is another view of the working end of FIG. 6F.

FIG. 6H is schematic view of a working end with a balloon.

FIG. 6I is schematic view of an articulating working end.

DETAILED DESCRIPTION OF THE INVENTION

As used in the specification, "a" or "an" means one or more. As used in the claim(s), when used in conjunction with the word "comprising", the words "a" or "an" mean one or more. As used herein, "another" means as least a second or more. "Substantially" or "substantial" mean largely but not entirely. For example, substantially may mean about 10% to about 99.999, about 25% to about 99.999% or about 50% to about 99.999%.

Figure 1A:
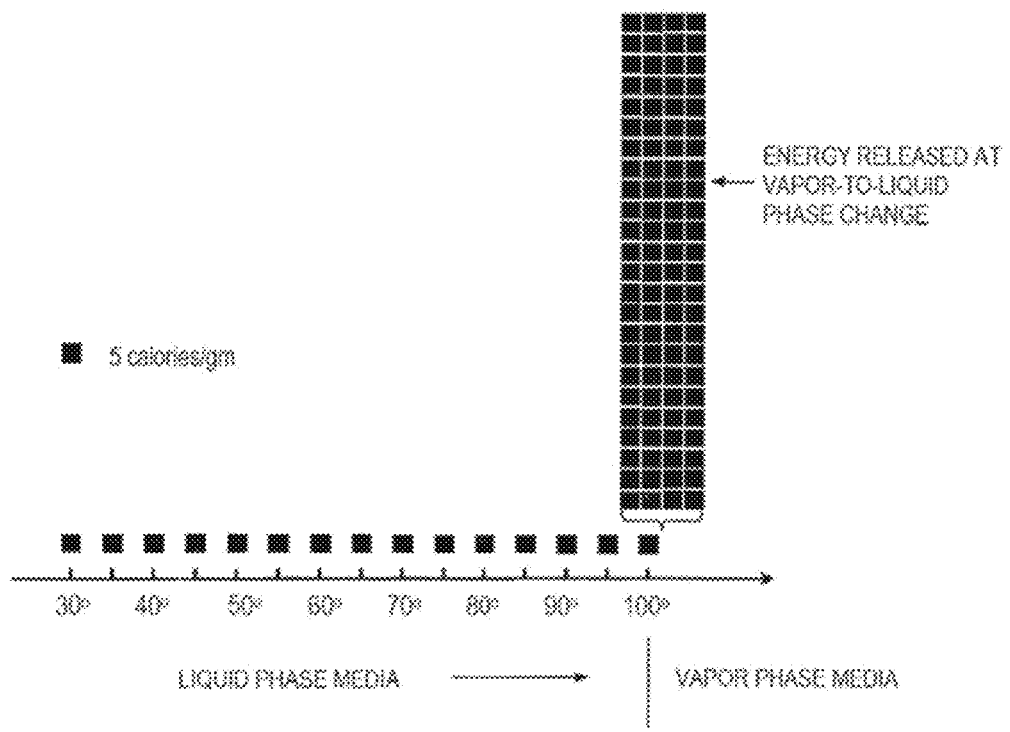
FIG. 1A is a graphical depiction of the quantity of energy needed to achieve the heat of vaporization of water.
Figure 1B:
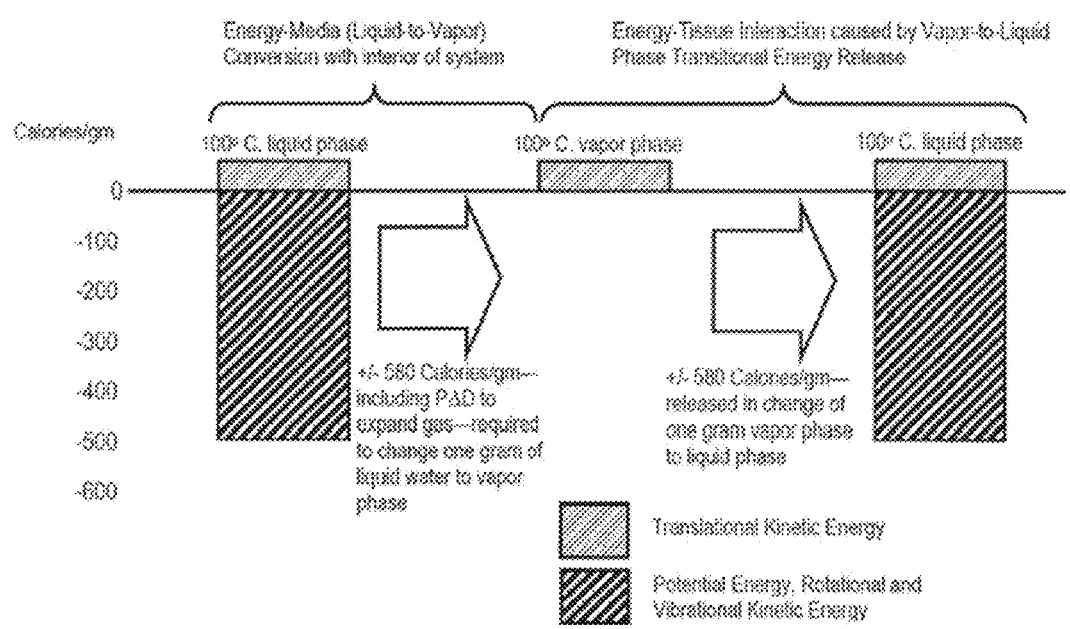
FIG. 1B is a diagram of phase change energy release that underlies a system and method of the invention.

In general, the thermally-mediated treatment method comprises causing a vapor-to-liquid phase state change in a selected media at a targeted tissue site thereby applying thermal energy substantially equal to the heat of vaporization of the selected media to the tissue site. The thermally-mediated therapy can be delivered to tissue by such vapor-to-liquid phase transitions, or "internal energy" releases, about the working surfaces of several types of instruments for ablative treatments of soft tissue. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of such energy in a controlled media-tissue interaction solves many of the vexing problems associated with energy-tissue interactions in Rf, laser and ultrasound modalities. The apparatus of the invention provides a vaporization chamber in the interior of an instrument, in an instrument's working end or in a source remote from the instrument end. A source provides liquid media to the interior vaporization chamber wherein energy is applied to create a selected volume of vapor media. In the process of the liquid-to-vapor phase transition of a liquid media, for example water, large amounts of energy are added to overcome the cohesive forces between molecules in the liquid, and an additional amount of energy is required to expand the liquid 1000+ percent (PAD) into a resulting vapor phase (see FIG. 1A). Conversely, in the vapor-to-liquid transition, such energy will be released at the phase transition at the interface with the targeted tissue site. That is, the heat of vaporization is released at the interface when the media transitions from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy at the interface with the targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. in FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media interaction within an interior vaporization chamber of medical thermotherapy system. The initial, ascendant energy-media interaction delivers energy sufficient to achieve the heat of vaporization of a selected liquid media, such as water or saline solution, within an interior of the system. This aspect of the technology requires a highly controlled energy source wherein a computer controller may need to modulated energy application between very large energy densities to initially surpass the latent heat of vaporization with some energy sources (e.g. a resistive heat source, an Rf energy source, a light energy source, a microwave energy source, an ultrasound source and/or an inductive heat source) and potential subsequent lesser energy densities for maintaining a high vapor quality. Additionally, a controller must control the pressure of liquid flows for replenishing the selected liquid media at the required rate and optionally for controlling propagation velocity of the vapor phase media from the working end surface of the instrument. In use, the method of the invention comprises the controlled application of energy to achieve the heat of vaporization as in FIG. 1A and the controlled vapor-to-liquid phase transition and vapor exit pressure to thereby control the interaction of a selected volume of vapor at the interface with tissue. The vapor-to-liquid phase transition can deposit 400, 500, 600 or more cal/gram within the targeted tissue site to perform the thermal ablation with the vapor in typical pressures and temperatures.

Treatment Liquid Source, Energy Source, Controller

Figure 2:
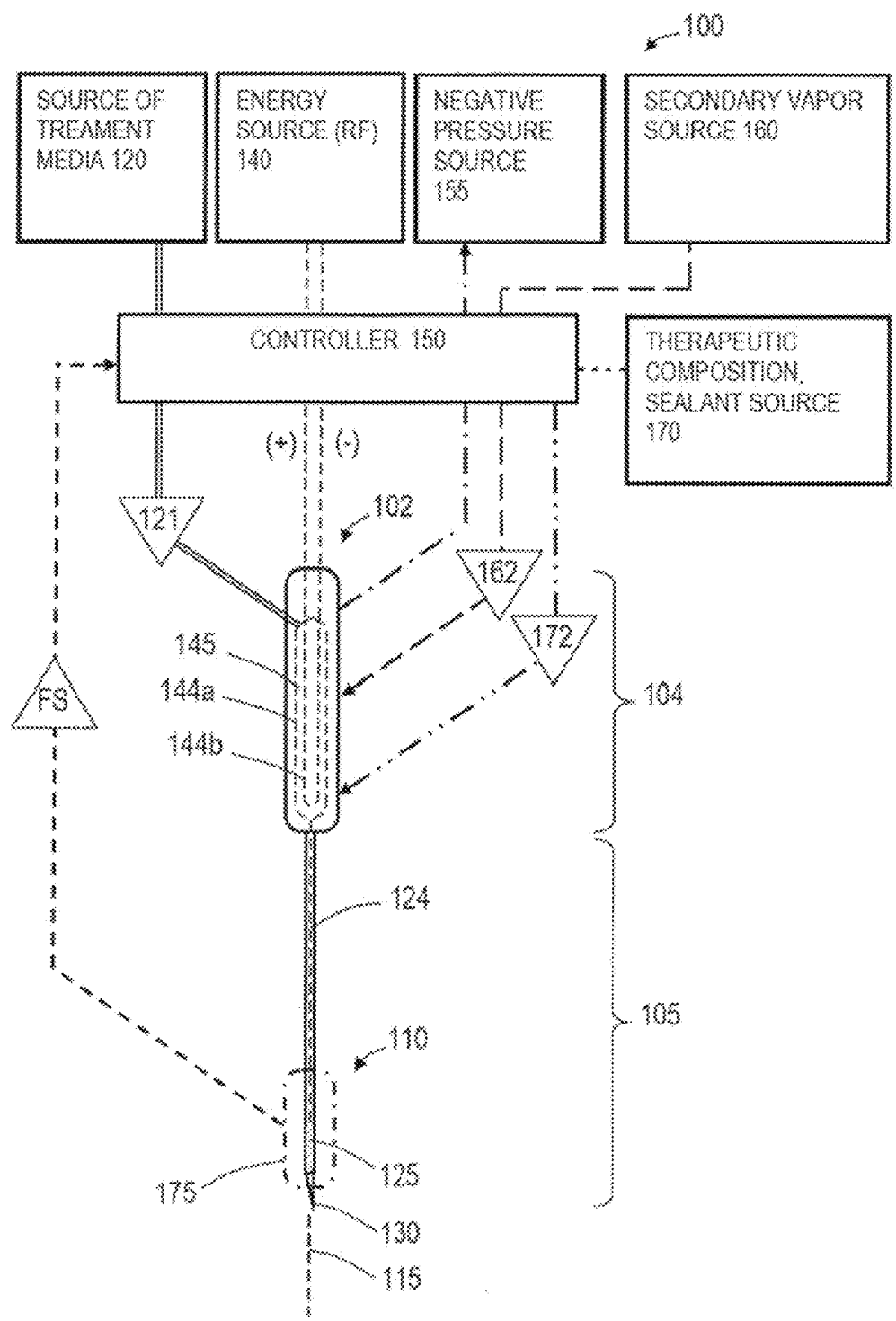
FIG. 2 shows a schematic view of a medical system that is adapted for treating a target region of tissue.

Referring to FIG. 2, a schematic view of medical system 100 of the present invention is shown that is adapted for treating a tissue target, wherein the treatment comprises an ablation or thermotherapy and the tissue target can comprise any mammalian soft tissue to be ablated, sealed, contracted, coagulated, damaged or treated to elicit an immune response. The system 100 includes an instrument or probe body 102 with a proximal handle end 104 and an extension portion 105 having a distal or working end indicated at 110. In one embodiment depicted in FIG. 2, the handle end 104 and extension portion 105 generally extend about longitudinal axis 115. In the embodiment of FIG. 2, the extension portion 105 is a substantially rigid tubular member with at least one flow channel therein, but the scope of the invention encompasses extension portions 105 of any mean diameter and any axial length, rigid or flexible, suited for treating a particular tissue target. In one embodiment, a rigid extension portion 105 can comprise a 20 Ga. to 40 Ga. needle with a short length for thermal treatment of a patient's cornea or a somewhat longer length for treating a patient's retina. In another embodiment, an elongate extension portion 105 of a vapor delivery tool can comprise a single needle or a plurality of needles having suitable lengths for tumor or soft tissue ablation in a liver, breast, gall bladder, prostate, bone and the like. In another embodiment, an elongate extension portion 105 can comprise a flexible catheter for introduction through a body lumen to access at tissue target, with a diameter ranging from about 1 to 10 mm. In another embodiment, the extension portion 105 or working end 110 can be articulatable, deflectable or deformable. The probe handle end 104 can be configured as a hand-held member, or can be configured for coupling to a robotic surgical system. In another embodiment, the working end 110 carries an openable and closeable structure for capturing tissue between first and second tissue-engaging surfaces, which can comprise actuatable components such as one or more clamps, jaws, loops, snares and the like. The proximal handle end 104 of the probe can carry various actuator mechanisms known in the art for actuating components of the system 100, and/or one or more footswitches can be used for actuating components of the system.

As can be seen in FIG. 2, the system 100 further includes a source 120 of a flowable liquid treatment media 121 that communicates with a flow channel 124 extending through the probe body 102 to at least one outlet 125 in the working end 110. The outlet 125 can be singular or multiple and have any suitable dimension and orientation as will be described further below. The distal tip 130 of the probe can be sharp for penetrating tissue, or can be blunt-tipped or open-ended with outlet 125. Alternatively, the working end 110 can be configured in any of the various embodiments shown in FIGS. 6A-6M and described further below.

In one embodiment shown in FIG. 2, an RF energy source 140 is operatively connected to a thermal energy source or emitter (e.g., opposing polarity electrodes 144a, 144b) in interior chamber 145 in the proximal handle end 104 of the probe for converting the liquid treatment media 121 from a liquid phase media to a non-liquid vapor phase media 122 with a heat of vaporization in the range of 60° C. to 200° C., or 80° C. to 120° C. A vaporization system using Rf energy and opposing polarity electrodes is disclosed in co-pending U.S. patent application Ser. No. 11/329,381 which is incorporated herein by reference. Another embodiment of vapor generation system is described in below in the Section titled "INDUCTIVE VAPOR GENERATION SYSTEMS". In any system embodiment, for example in the system of FIG. 2, a controller 150 is provided that comprises a computer control system configured for controlling the operating parameters of inflows of liquid treatment media source 120 and energy applied to the liquid media by an energy source to cause the liquid-to-vapor conversion. The vapor generation systems described herein can consistently produce a high quality vapor having a temperature of at least 80° C., 100° C. 120° C., 140° C. and 160° C.

As can be seen in FIG. 2, the medical system 100 can further include a negative pressure or aspiration source indicated at 155 that is in fluid communication with a flow channel in probe 102 and working end 110 for aspirating treatment vapor media 122, body fluids, ablation by-products, tissue debris and the like from a targeted treatment site, as will be further described below. In FIG. 2, the controller 150 also is capable of modulating the operating parameters of the negative pressure source 155 to extract vapor media 122 from the treatment site or from the interior of the working end 110 by means of a recirculation channel to control flows of vapor media 122 as will be described further below.

In another embodiment, still referring to FIG. 2, medical system 100 further includes secondary media source 160 for providing an inflow of a second media, for example a biocompatible gas such as $CO_2$. In one method, a second media that includes at least one of depressurized $CO_2$, $N_2$, $O_2$ or $H_2O$ can be introduced and combined with the vapor media 122. This second media 162 is introduced into the flow of non-ionized vapor media for lowering the mass average temperature of the combined flow for treating tissue. In another embodiment, the medical system 100 includes a source 170 of a therapeutic or pharmacological agent or a sealant composition indicated at 172 for providing an additional treatment effect in the target tissue. In FIG. 2, the controller indicated at 150 also is configured to modulate the operating parameters of source 160 and 170 to control inflows of a secondary vapor 162 and therapeutic agents, sealants or other compositions indicated at 172.

In FIG. 2, it is further illustrated that a sensor system 175 is carried within the probe 102 for monitoring a parameter of the vapor media 122 to thereby provide a feedback signal FS to the controller 150 by means of feedback circuitry to thereby allow the controller to modulate the output or operating parameters of treatment media source 120, energy source 140, negative pressure source 155, secondary media source 160 and therapeutic agent source 170. The sensor system 175 is further described below, and in one embodiment comprises a flow sensor to determine flows or the lack of a vapor flow. In another embodiment, the sensor system 175 includes a temperature sensor. In another embodiment, sensor system 175 includes a pressure sensor. In another embodiment, the sensor system 175 includes a sensor arrangement for determining the quality of the vapor media, e.g., in terms or vapor saturation or the like. The sensor systems will be described in more detail below.

Figure 3:
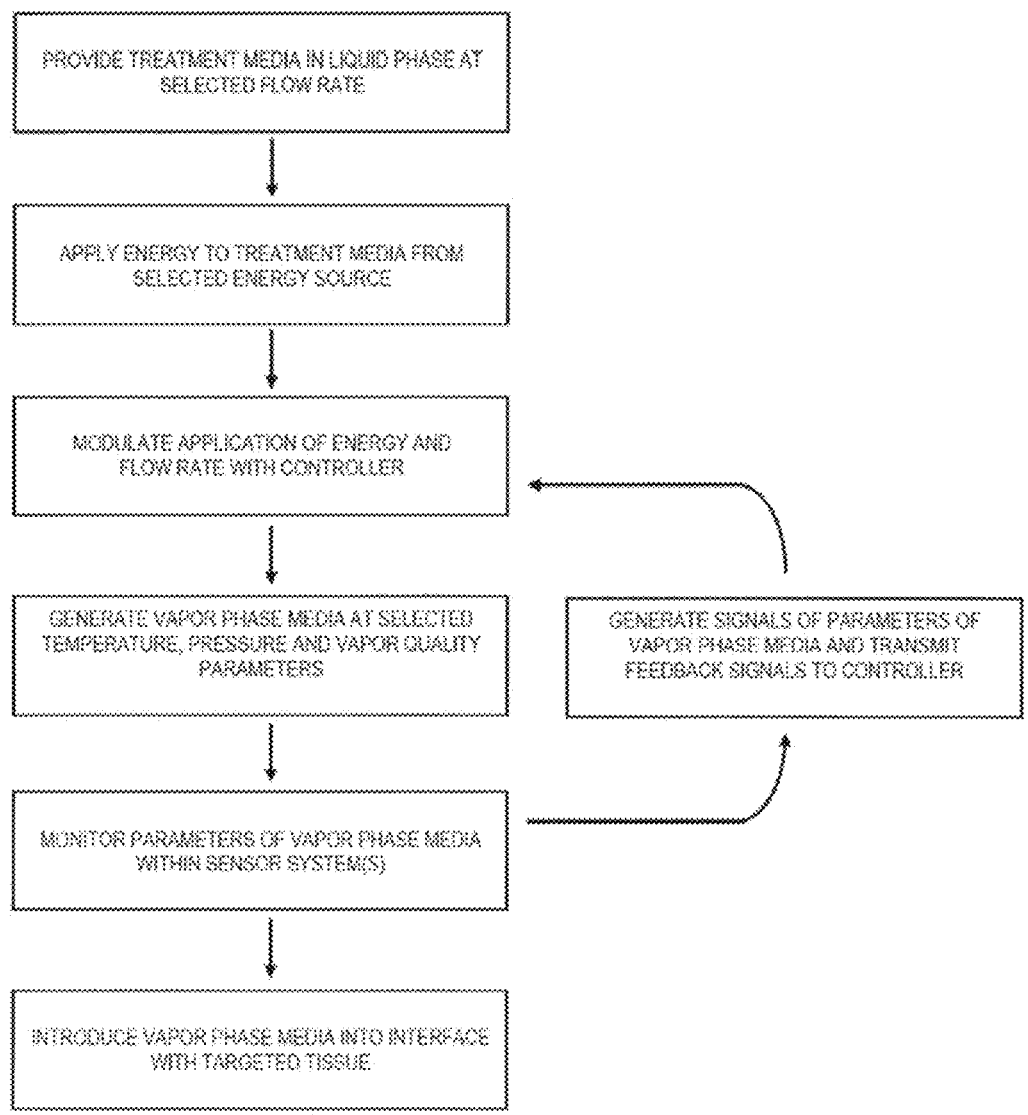
FIG. 3 is a block diagram of a control method of the invention.

Now turning to FIGS. 2 and 3, the controller 150 is capable of all operational parameters of system 100, including modulating the operational parameters in response to preset values or in response to feedback signals FS from sensor system(s) 175 within the system 100 and probe working end 110. In one embodiment, as depicted in the block diagram of FIG. 3, the system 100 and controller 150 are capable of providing or modulating an operational parameter comprising a flow rate of liquid phase treatment media 122 from pressurized source 120, wherein the flow rate is within a range from about 0.001 to 20 ml/min, 0.010 to 10 ml/min or 0.050 to 5 ml/min. The system 100 and controller 150 are further capable of providing or modulating another operational parameter comprising the inflow pressure of liquid phase treatment media 121 in a range from 0.5 to 1000 psi, 5 to 500 psi, or 25 to 200 psi. The system 100 and controller 150 are further capable of providing or modulating another operational parameter comprising a selected level of energy capable of converting the liquid phase media into a non-liquid, non-ionized gas phase media, wherein the energy level is within a range of about 5 to 2,500 watts; 10 to 1,000 watts or 25 to 500 watts. The system 100 and controller 150 are capable of applying the selected level of energy to provide the phase conversion in the treatment media over an interval ranging from 0.1 second to 10 minutes; 0.5 seconds to 5 minutes, and 1 second to 60 seconds. The system 100 and controller 150 are further capable of controlling parameters of the vapor phase media including the flow rate of non-ionized vapor media proximate an outlet 125, the pressure of vapor media 122 at the outlet, the temperature or mass average temperature of the vapor media, and the quality of vapor media as will be described further below.

Figure 4A:
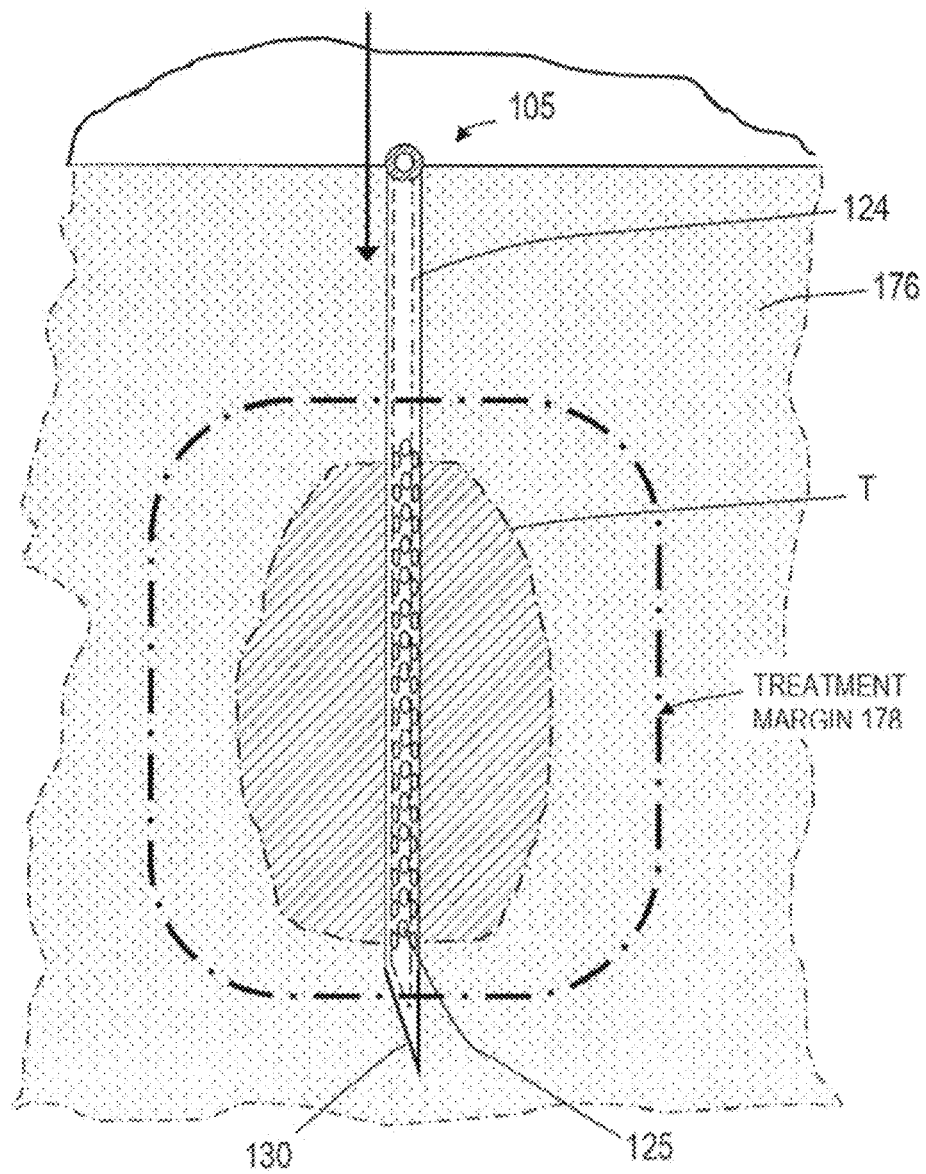
FIG. 4A is an illustration of the working end of FIG. 2 being introduced into soft tissue to treat a targeted tissue volume.
Figure 4B:
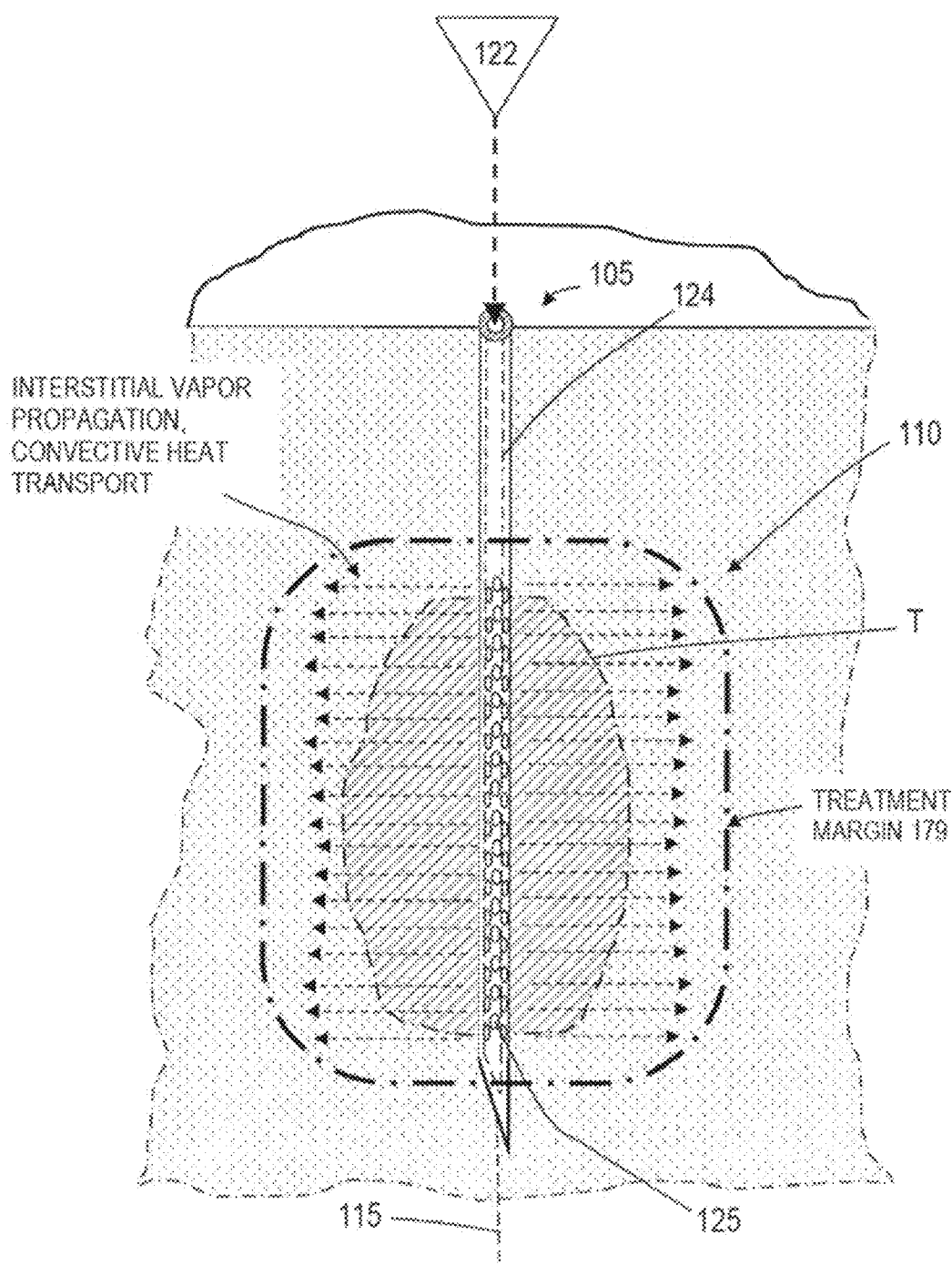
FIG. 4B is an illustration of the working end of FIG. 4A showing the propagation of vapor media in tissue in a method of use in ablating a tumor.

FIGS. 4A and 4B illustrate a working end 110 of the system 100 of FIG. 2 and a method of use. As can be seen in FIG. 4A, a working end 110 is singular and configured as a needle-like device for penetrating into and/or through a targeted tissue T such as a tumor in a tissue volume 176. The tumor can be benign, malignant, hyperplastic or hypertrophic tissue, for example, in a patient's breast, uterus, lung, liver, kidney, gall bladder, stomach, pancreas, colon, GI tract, bladder, prostate, bone, vertebra, eye, brain or other tissue. In one embodiment of the invention, the extension portion 104 is made of a metal, for example, stainless steel. Alternatively or additionally, at least some portions of the extension portion can be fabricated of a polymer material such as PEEK, PTFE, Nylon or polypropylene. Also optionally, one or more components of the extension portion are formed of coated metal, for example, a coating with Teflon® to reduce friction upon insertion and to prevent tissue sticking following use. In one embodiment at in FIG. 4A, the working end 110 includes a plurality of outlets 125 that allow vapor media to be ejected in all radial directions over a selected treatment length of the working end. In another embodiment, the plurality of outlets can be symmetric or asymmetric axially or angularly about the working end 110.

Figure 5:
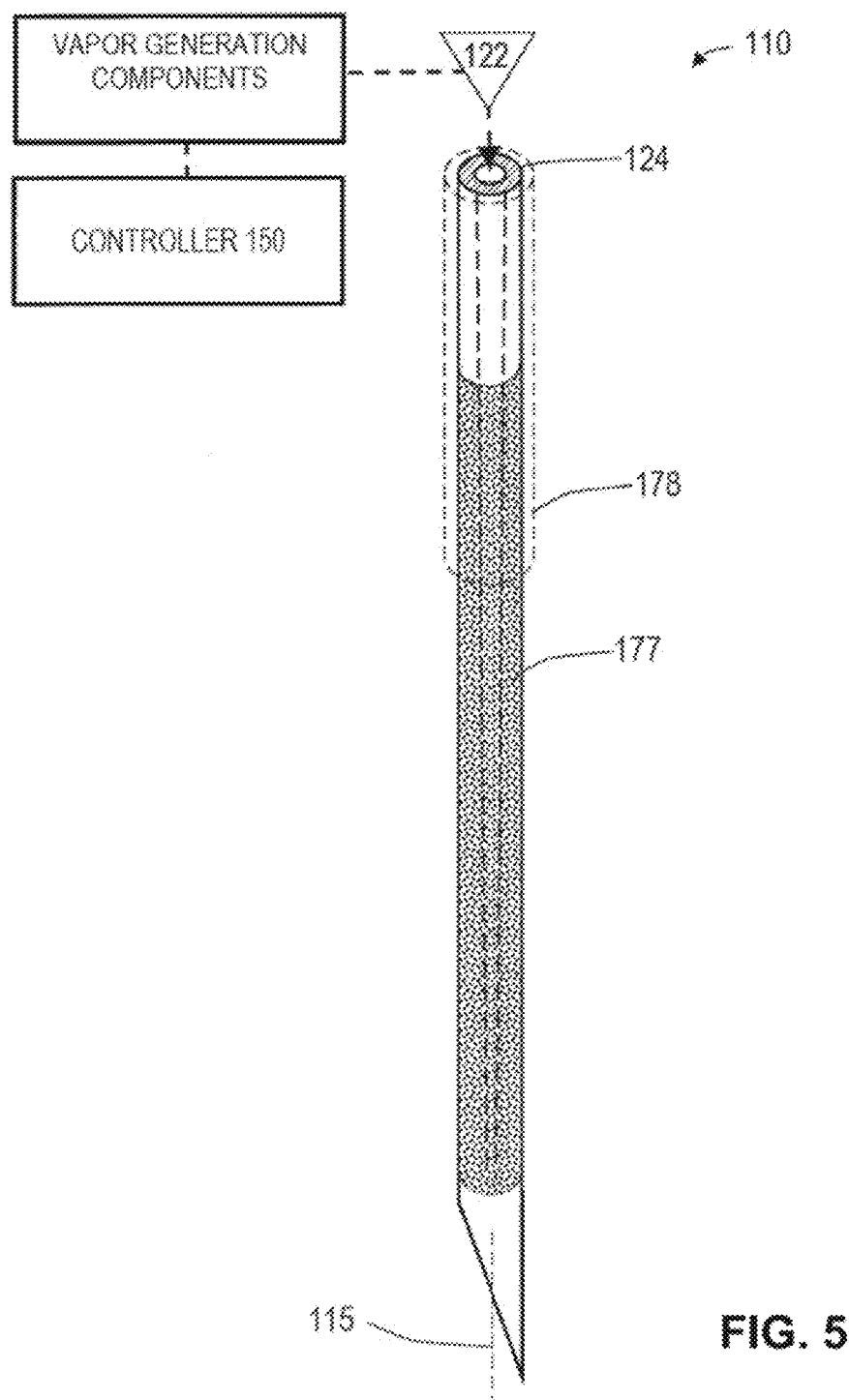
FIG. 5 is an illustration of a working end similar to FIGS. 4A-4B with vapor outlets comprising microporosities in a porous wall.

In one embodiment, the outer diameter of extension portion 105 or working end 110 is, for example, 0.2 mm, 0.5 mm, 1 mm, 2 mm, 5 mm or an intermediate, smaller or larger diameter. Optionally, the outlets can comprise microporosities 177 in a porous material as illustrated in FIG. 5 for diffusion and distribution of vapor media flows about the surface of the working end. In one such embodiment, such porosities provide a greater restriction to vapor media outflows than adjacent targeted tissue, which can vary greatly in vapor permeability. In this case, such microporosities insure that vapor media outflows will occur substantially uniformly over the surface of the working end. Optionally, the wall thickness of the working end 110 is from 0.05 to 0.5 mm. Optionally, the wall thickness decreases or increases towards the distal sharp tip 130 (FIG. 5). In one embodiment, the dimensions and orientations of outlets 125 are selected to diffuse and/or direct vapor media propagation into targeted tissue T and more particularly to direct vapor media into all targeted tissue to cause extracellular vapor propagation and thus convective heating of the target tissue as indicated in FIG. 4B. As shown in FIGS. 4A-4B, the shape of the outlets 125 can vary, for example, round, ellipsoid, rectangular, radially and/or axially symmetric or asymmetric. As shown in FIG. 5, a sleeve 178 can be advanced or retracted relative to the outlets 125 to provide a selected exposure of such outlets to provide vapor injection over a selected length of the working end 110. Optionally, the outlets can be oriented in various ways, for example so that vapor media 122 is ejected perpendicular to a surface of working end 110, or ejected is at an angle relative to the axis 115 or angled relative to a plane perpendicular to the axis. Optionally, the outlets can be disposed on a selected side or within a selected axial portion of working end, wherein rotation or axial movement of the working end will direct vapor propagation and energy delivery in a selected direction. In another embodiment, the working end 110 can be disposed in a secondary outer sleeve that has apertures in a particular side thereof for angular/axial movement in targeted tissue for directing vapor flows into the tissue.

FIG. 4B illustrates the working end 110 of system 100 ejecting vapor media from the working end under selected operating parameters, for example a selected pressure, vapor temperature, vapor quantity, vapor quality and duration of flow. The duration of flow can be a selected pre-set or the hyperechoic aspect of the vapor flow can be imaged by means of ultrasound to allow the termination of vapor flows by observation of the vapor plume relative to targeted tissue T. As depicted schematically in FIG. 4B, the vapor can propagate extracellularly in soft tissue to provide intense convective heating as the vapor collapses into water droplets, which results in effective tissue ablation and cell death. As further depicted in FIG. 4B, the tissue is treated to provide an effective treatment margin 179 around a targeted tumorous volume. The vapor delivery step is continuous or can be repeated at a high repetition rate to cause a pulsed form of convective heating and thermal energy delivery to the targeted tissue. The repetition rate vapor flows can vary, for example with flow duration intervals from 0.01 to 20 seconds and intermediate off intervals from 0.01 to 5 seconds or intermediate, larger or smaller intervals.

In an exemplary embodiment as shown in FIGS. 4A-4B, the extension portion 105 can be a unitary member such as a needle. In another embodiment, the extension portion 105 or working end 110 can be a detachable flexible body or rigid body, for example of any type selected by a user with outlet sizes and orientations for a particular procedure with the working end attached by threads or Luer fitting to a more proximal portion of probe 102.

Figure 6A:
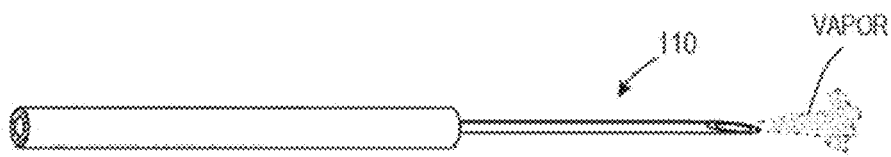
FIG. 6A is schematic view of a needle-type working end of a vapor delivery tool for applying energy to tissue.
Figure 6B:
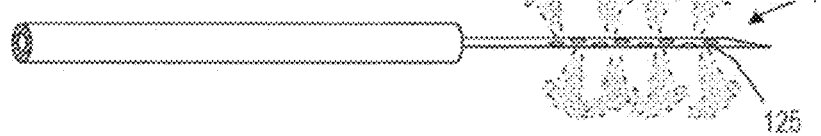
FIG. 6B is schematic view of an alternative needle-type working end similar to FIG. 6A.
Figure 6C:
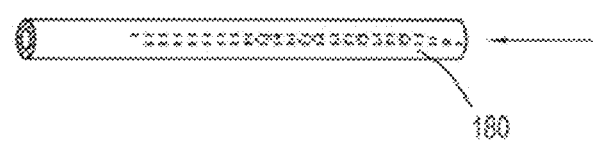
FIG. 6C is schematic view of a retractable needle-type working end similar to FIG. 6B.
Figure 6D:
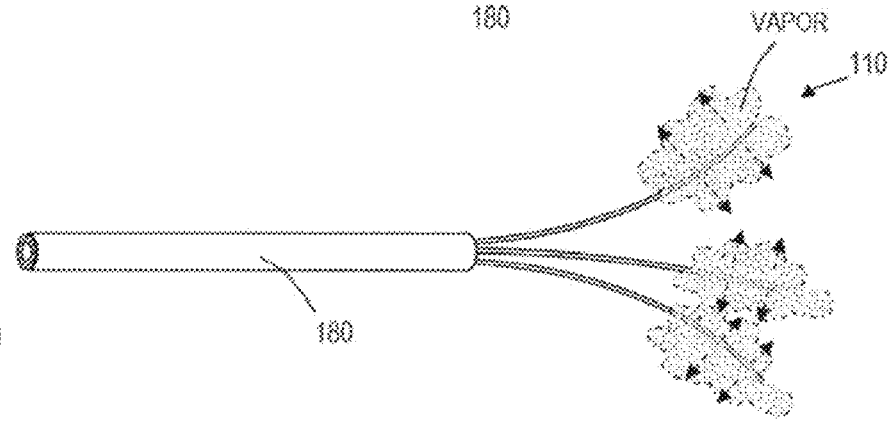
FIG. 6D is schematic view of working end with multiple shape-memory needles.
Figure 6E:
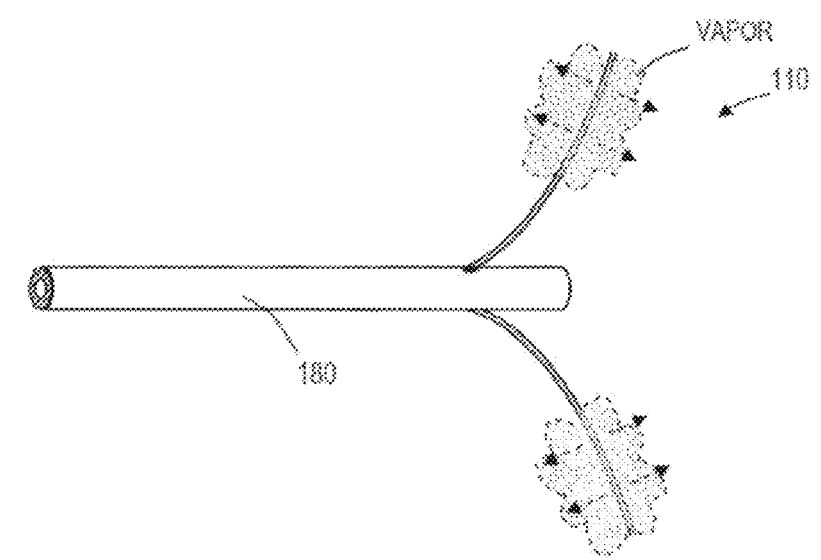
FIG. 6E is schematic view of a working end with deflectable needles.

In other embodiments, the working end 110 can comprise needles with terminal outlets or side outlets as shown in FIGS. 6A-6B. The needle of FIGS. 6A and 6B can comprise a retractable needle as shown in FIG. 6C capable of retraction into probe or sheath 180 for navigation of the probe through a body passageway or for blocking a portion of the vapor outlets 125 to control the geometry of the vapor-tissue interface. In another embodiment shown in FIG. 6D, the working end 110 can have multiple retractable needles that are of a shape memory material. In another embodiment as depicted in FIG. 6E, the working end 110 can have at least one deflectable and retractable needle that deflects relative to an axis of the probe 180 when advanced from the probe. In another embodiment, the working end 110 as shown in FIGS. 6F-6G can comprise a dual sleeve assembly wherein vapor-carrying inner sleeve 181 rotates within outer sleeve 182 and wherein outlets in the inner sleeve 181 only register with outlets 125 in outer sleeve 182 at selected angles of relative rotation to allow vapor to exit the outlets. This assembly thus provides for a method of pulsed vapor application from outlets in the working end. The rotation can be from about 1 rpm to 1000 rpm.

In another embodiment of FIG. 6H, the working end 110 has a heat applicator surface with at least one vapor outlet 125 and at least one expandable member 183 such as a balloon for positioning the heat applicator surface against targeted tissue. In another embodiment of FIG. 6I, the working end can be a flexible material that is deflectable by a pull-wire as is known in the art. The embodiments of FIGS. 6H and 6I have configurations for use in treating atrial fibrillation, for example in pulmonary vein ablation.

Figure 6J:
FIG. 6J is schematic view of an alternative working end with RF electrodes.
Figure 6K:
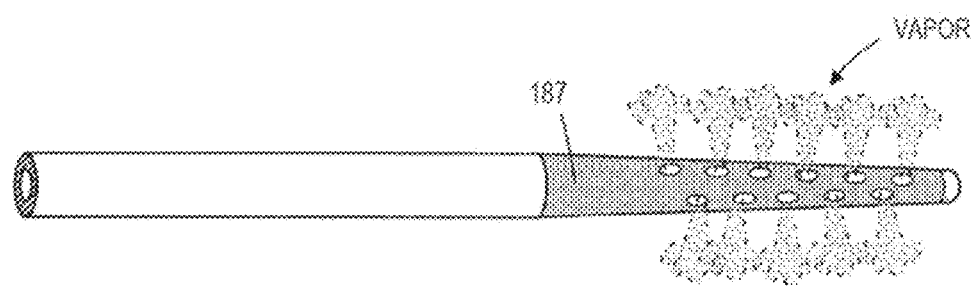
FIG. 6K is schematic view of an alternative working end with a resistive heating element.
Figure 6L:
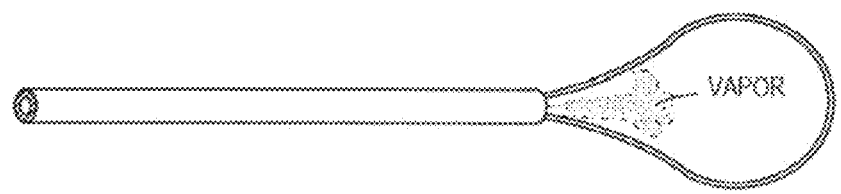
FIG. 6L is schematic view of a working end with a tissue-capturing loop.
Figure 6M:
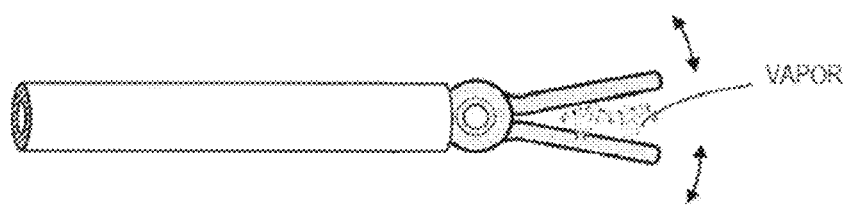
FIG. 6M is schematic view of an alternative working end with jaws for capturing and delivering vapor to tissue.

In another embodiment of FIG. 6J, the working end 110 includes additional optional heat applicator means which can comprise a mono-polar electrode cooperating with a ground pad or bi-polar electrodes 184a and 184b for applying energy to tissue. In FIG. 6K, the working end 110 includes resistive heating element 187 for applying energy to tissue. FIG. 6L depicts a snare for capturing tissue to be treated with vapor and FIG. 6M illustrates a clamp or jaw structure. The working end 110 of FIG. 6M includes means actuatable from the handle for operating the jaws.

Sensors for Vapor Flows, Temperature, Pressure, Quality

Figure 7:
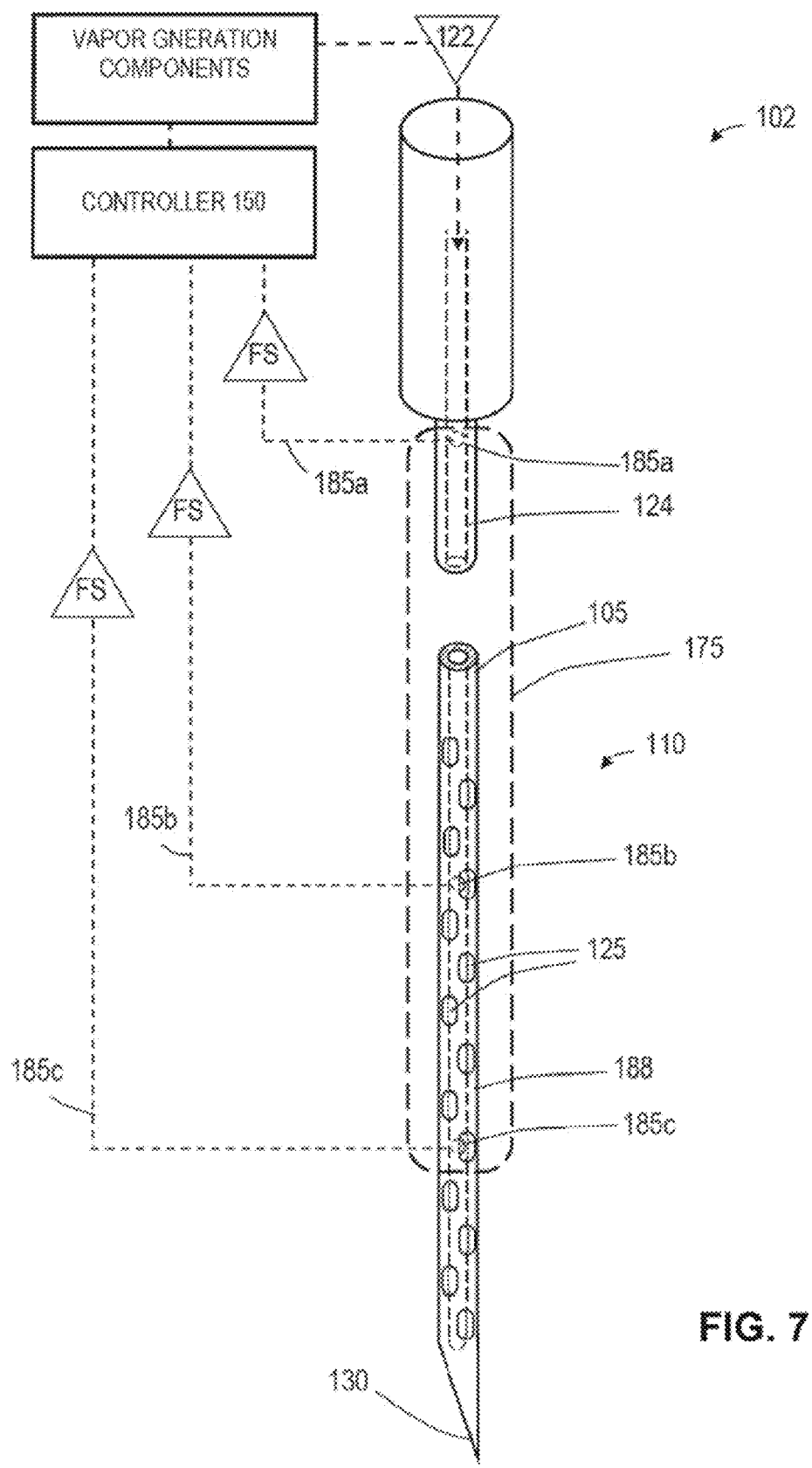
FIG. 7 is schematic view of an alternative working end with jaws for capturing and delivering vapor to tissue.

Referring to FIG. 7, one embodiment of sensor system 175 is shown that is carried by working end 110 of the probe 102 depicted in FIG. 2 for determining a first vapor media flow parameter, which can consist of determining whether the vapor flow is in an "on" or "off" operating mode. The working end 110 of FIG. 7 comprises a sharp-tipped needle suited for needle ablation of any neoplasia or tumor tissue, such as a benign or malignant tumor as described previously, but can also be any other form of vapor delivery tool. The needle can be any suitable gauge and in one embodiment has a plurality of vapor outlets 125. In a typical treatment of targeted tissue, it is important to provide a sensor and feedback signal indicating whether there is a flow, or leakage, of vapor media 122 following treatment or in advance of treatment when the system is in "off" mode. Similarly, it is important to provide a feedback signal indicating a flow of vapor media 122 when the system is in "on" mode. In the embodiment of FIG. 7, the sensor comprises at least one thermocouple or other temperature sensor indicated at 185a, 185b and 185c that are coupled to leads (indicated schematically at 186a, 186b and 186c) for sending feedback signals to controller 150. The temperature sensor can be a singular component or can be plurality of components spaced apart over any selected portion of the probe and working end. In one embodiment, a feedback signal of any selected temperature from any thermocouple in the range of the heat of vaporization of treatment media 122 would indicate that flow of vapor media, or the lack of such a signal would indicate the lack of a flow of vapor media. The sensors can be spaced apart by at least 0.05 mm, 1 mm, 5 mm, 10 mm and 50 mm. In other embodiments, multiple temperature sensing event can be averaged over time, averaged between spaced apart sensors, the rate of change of temperatures can be measured and the like. In one embodiment, the leads 186a, 186b and 186c are carried in an insulative layer of wall 188 of the extension member 105. The insulative layer of wall 188 can include any suitable polymer or ceramic for providing thermal insulation. In one embodiment, the exterior of the working end also is also provided with a lubricious material such as Teflon® which further insures against any tissue sticking to the working end 110.

Still referring to FIG. 7, a sensor system 175 can provide a different type of feedback signal FS to indicate a flow rate or vapor media based on a plurality of temperature sensors spaced apart within flow channel 124. In one embodiment, the controller 150 includes algorithms capable of receiving feedback signals FS from at least first and second thermocouples (e.g., 185a and 185c) at very high data acquisition speeds and compare the difference in temperatures at the spaced apart locations. The measured temperature difference, when further combined with the time interval following the initiation of vapor media flows, can be compared against a library to thereby indicate the flow rate.

Figure 8:
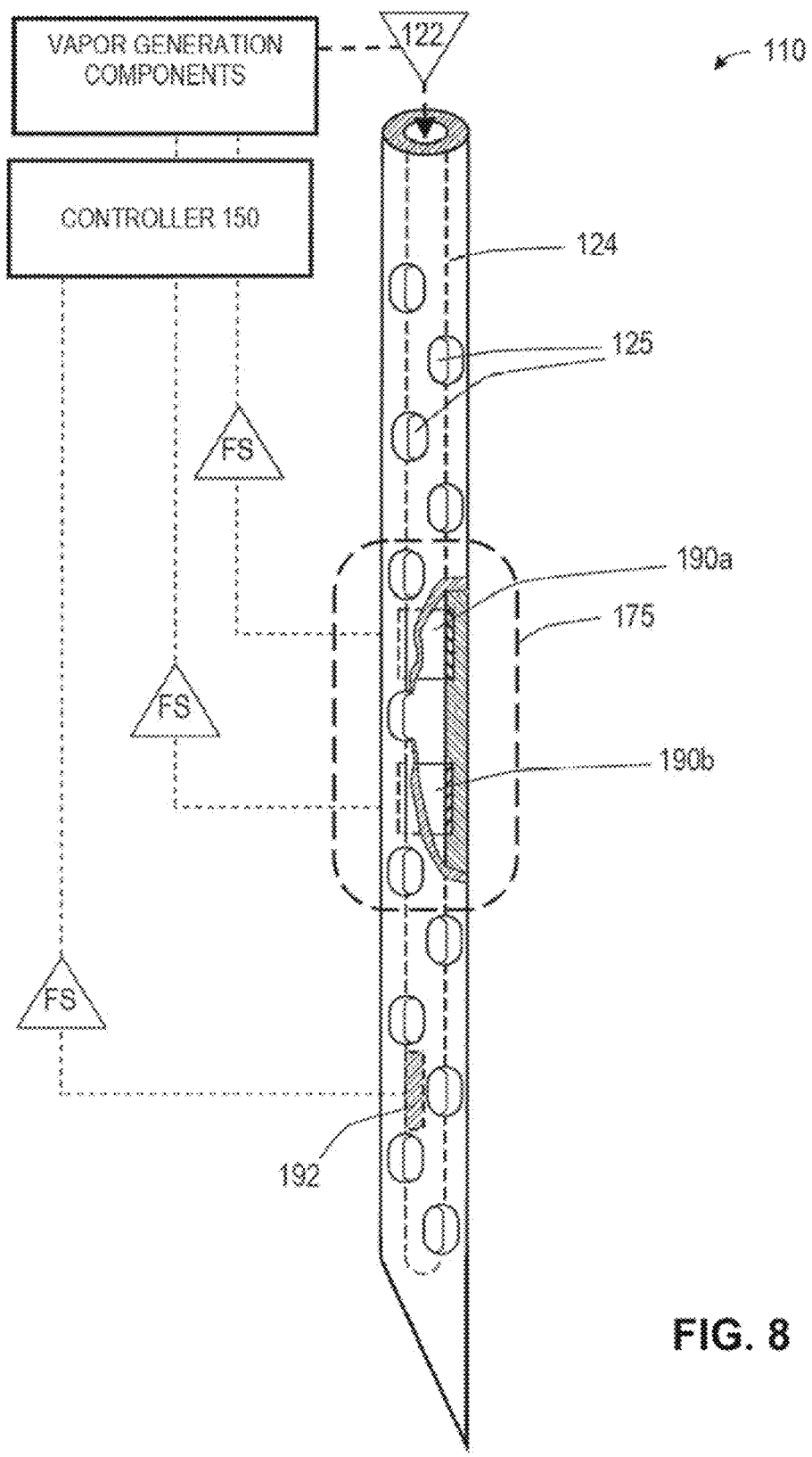
FIG. 8 is schematic view of an alternative working end with jaws for capturing and delivering vapor to tissue.

Another embodiment of sensor system 175 in a similar working end 110 is depicted in FIG. 8, wherein the sensor is configured for indicating vapor quality—in this case based on a plurality of spaced apart electrodes 190a and 190b coupled to controller 150 and an electrical source (not shown). In this embodiment, a current flow is provided within a circuit to the spaced apart electrodes 190a and 190b and during vapor flows within channel 124 the impedance will vary depending on the vapor quality or saturation, which can be processed by algorithms in controller 150 and can be compared to a library of impedance levels, flow rates and the like to thereby determine vapor quality. It is important to have a sensor to provide feedback of vapor quality, which determines how much energy is being carried by a vapor flow. The term "vapor quality" is herein used to describe the percentage of the flow that is actually water vapor as opposed to water droplets that is not phase-changed. In another embodiment (not shown) an optical sensor can be used to determine vapor quality wherein a light emitter and receiver can determine vapor quality based on transmissibility or reflectance of light relative to a vapor flow.

FIG. 8 further depicts a pressure sensor 192 in the working end 110 for providing a signal as to vapor pressure. In operation, the controller can receive the feedback signals FS relating to temperature, pressure and vapor quality to thereby modulate all other operating parameters described above to optimize flow parameters for a particular treatment of a target tissue, as depicted in FIG. 1. In one embodiment, a MEMS pressure transducer is used, which are known in the art. In another embodiment, a MEMS accelerometer coupled to a slightly translatable coating can be utilized to generate a signal of changes in flow rate, or a MEMS microphone can be used to compare against a library of acoustic vibrations to generate a signal of flow rates.

Inductive Vapor Generation Systems

Figure 9:
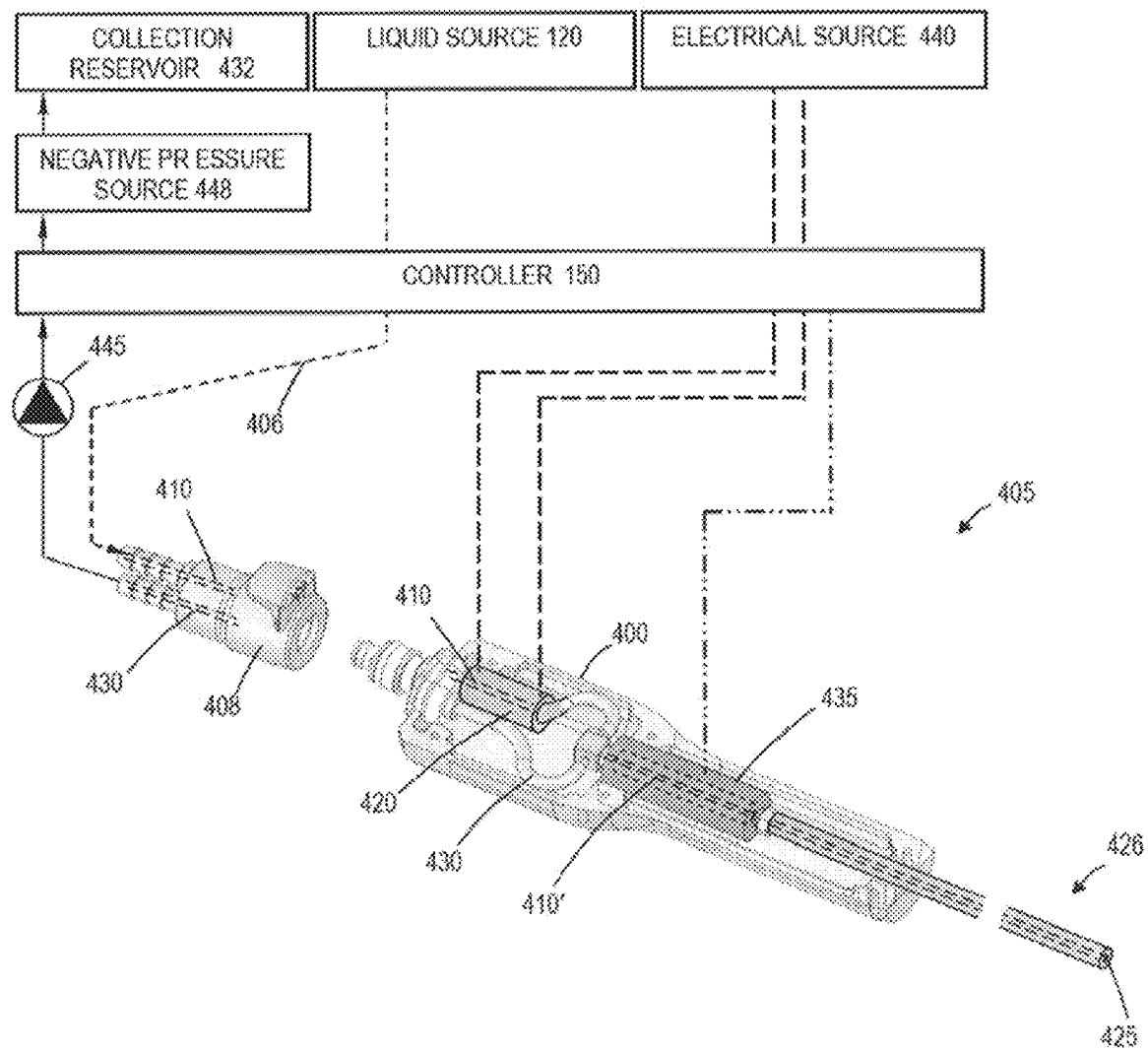
FIG. 9 is a partly disassembled view of a handle and inductive vapor generator system of the invention.
Figure 10:
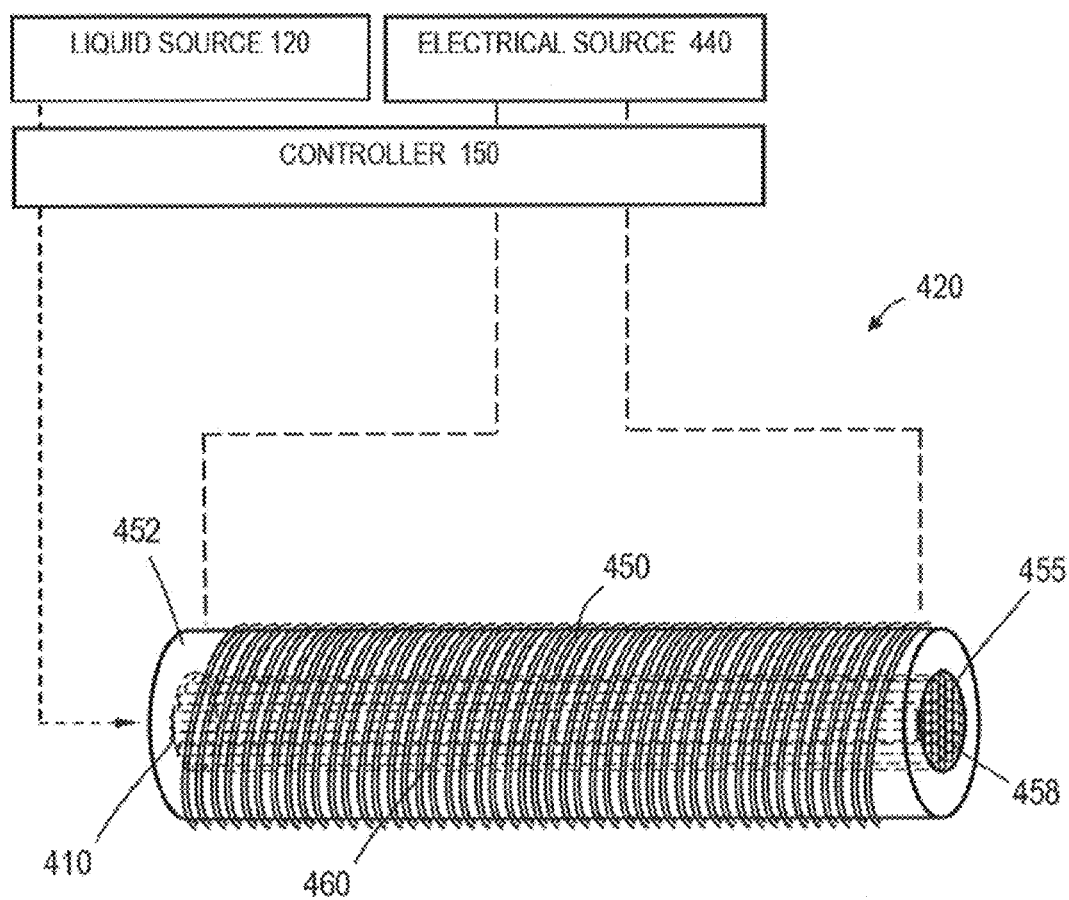
FIG. 10 is an enlarged schematic view of the inductive vapor generator of FIG. 9.

FIGS. 9 and 10 depict a vapor generation component that utilizes and an inductive heating system within a handle portion 400 of the probe or vapor delivery tool 405. In FIG. 9, it can be seen that a pressurized source of liquid media 120 (e.g., water or saline) is coupled by conduit 406 to a quick-connect fitting 408 to deliver liquid into a flow channel 410 extending through an inductive heater 420 in probe handle 400 to at least one outlet 425 in the working end 426. In one embodiment shown in FIG. 9, the flow channel 410 has a bypass or recirculation channel portion 430 in the handle or working end 426 that can direct vapor flows to a collection reservoir 432. In operation, a valve 435 in the flow channel 410 thus can direct vapor generated by inductive heater 420 to either flow channel portion 410' or the recirculation channel portion 430. In the embodiment of FIG. 10, the recirculation channel portion 430 also is a part of the quick-connect fitting 408.

In FIG. 9, it can be seen that the system includes a computer controller 150 that controls (i) the electromagnetic energy source 440 coupled to inductive heater 420, (ii) the valve 435 which can be an electrically-operated solenoid, (iii) an optional valve 445 in the recirculation channel 430 that can operate in unison with valve 435, and (iv) optional negative pressure source 448 operatively coupled to the e recirculation channel 430.

In general, the system of the invention provides a small handheld device including an assembly that utilized electromagnetic induction to turn a sterile water flow into superheated or dry vapor which can is propagated from at least one outlet in a vapor delivery tool to interface with tissue and thus ablate tissue. In one aspect of the invention, an electrically-conducting microchannel structure or other flow-permeable structure is provided and an inductive coil causes electric current flows in the structure. Eddies within the current create magnetic fields, and the magnetic fields oppose the change of the main field thus raising electrical resistance and resulting in instant heating of the microchannel or other flow-permeable structure. In another aspect of the invention, it has been found that corrosion-resistant microtubes of low magnetic 316 SS are best suited for the application, or a sintered microchannel structure of similar material. While magnetic materials can improve the induction heating of a metal because of ferromagnetic hysteresis, such magnetic materials (e.g. carbon steel) are susceptible to corrosion and are not optimal for generating vapor used to ablate tissue. In certain embodiments, the electromagnetic energy source 440 is adapted for inductive heating of a microchannel structure with a frequency in the range of 50 kHz to 2 Mhz, and more preferably in the range of 400 kHz to 500 kHz. While a microchannel structure is described in more detail below, it should be appreciated that the scope of the invention includes flow-permeable conductive structures selected from the group of woven filaments structures, braided filament structures, knit filaments structures, metal wool structures, porous structures, honeycomb structures and an open cell structures.

In general, a method of the invention comprises utilizing an inductive heater 420 of FIGS. 9-10 to instantly vaporize a treatment media such as de-ionized water that is injected into the heater at a flow rate of ranging from 0.001 to 20 ml/min, 0.010 to 10 ml/min, 0.050 to 5 mL/min., and to eject the resulting vapor into body structure to ablate tissue. The method further comprises providing an inductive heater 420 configured for a disposable had-held device (see FIG. 9) that is capable of generating a minimum water vapor that is at least 70% water vapor, 80% water vapor and 90% water vapor.

FIG. 10 is an enlarged schematic view of inductive heater 420 which includes at least one winding of inductive coil 450 wound about an insulative sleeve 452. The coil 450 is typically wound about a rigid insulative member, but also can comprise a plurality of rigid coil portions about a flexible insulator or a flexible coil about a flexible insulative sleeve. The coil can be in handle portion of a probe or in a working end of a probe such as a catheter. The inductive coil can extends in length at least 5 mm, 10 mm, 25 mm, 50 mm or 100 m.

In one embodiment shown schematically in FIG. 10, the inductive heater 420 has a flow channel 410 in the center of insulative sleeve 452 wherein the flows passes through an inductively heatable microchannel structure indicated at 455. The microchannel structure 455 comprises an assembly of metal hypotubes 458, for example consisting of thin-wall biocompatible stainless steel tube tightly packed in bore 460 of the assembly. The coil 450 can thereby inductively heat the metal walls of the microchannel structure 455 and the very large surface area of structure 455 in contact with the flow can instantly vaporize the flowable media pushed into the flow channel 410. In one embodiment, a ceramic insulative sleeve 452 has a length of 1.5" and outer diameter of 0.25" with a 0.104" diameter bore 460 therein. A total of thirty-two 316 stainless steel tubes 458 with 0.016" O.D., 0.010" I.D., and 0.003" wall are disposed in bore 460. The coil 450 has a length of 1.0" and comprises a single winding of 0.026" diameter tin-coated copper strand wire (optionally with ceramic or Teflon® insulation) and can be wound in a machined helical groove in the insulative sleeve 452. A 200 W RF power source 440 is used operating at 400 kHz with a pure sine wave. A pressurized sterile water source 120 comprises a computer controlled syringe that provides fluid flows of deionized water at a rate of 3 ml/min which can be instantly vaporized by the inductive heater 420. At the vapor exit outlet or outlets 125 in a working end, it has been found that various pressures are needed for various tissues and body cavities for optimal ablations, ranging from about 0.1 to 20 psi for ablating body cavities or lumens and about 1 psi to 100 psi for interstitial ablations.

Figure 11A:
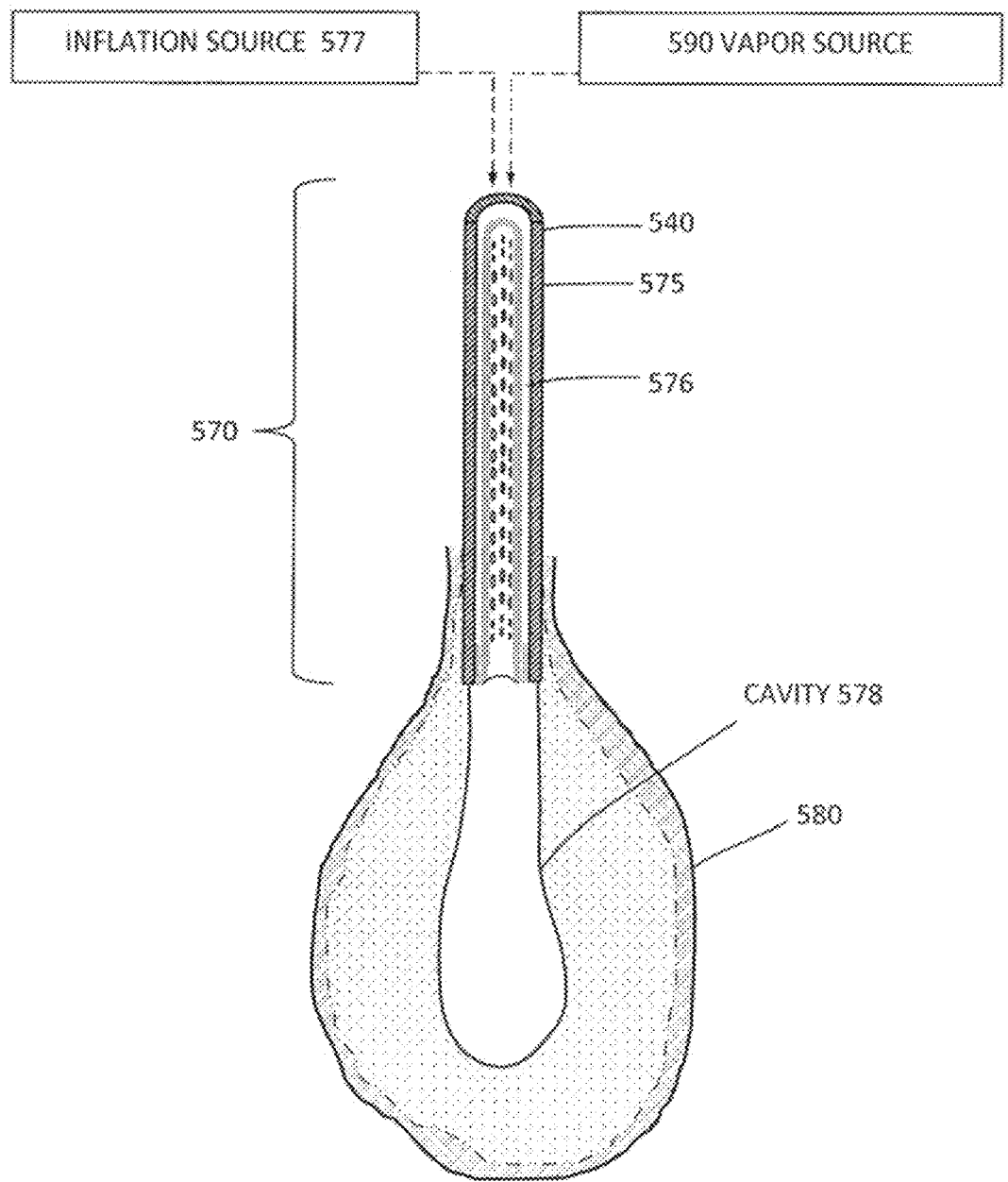
FIG. 11A is a sectional view of the working end of a vapor delivery tool comprising an introducer carrying an expandable structure for delivering vapor from outlets therein.
Figure 11B:
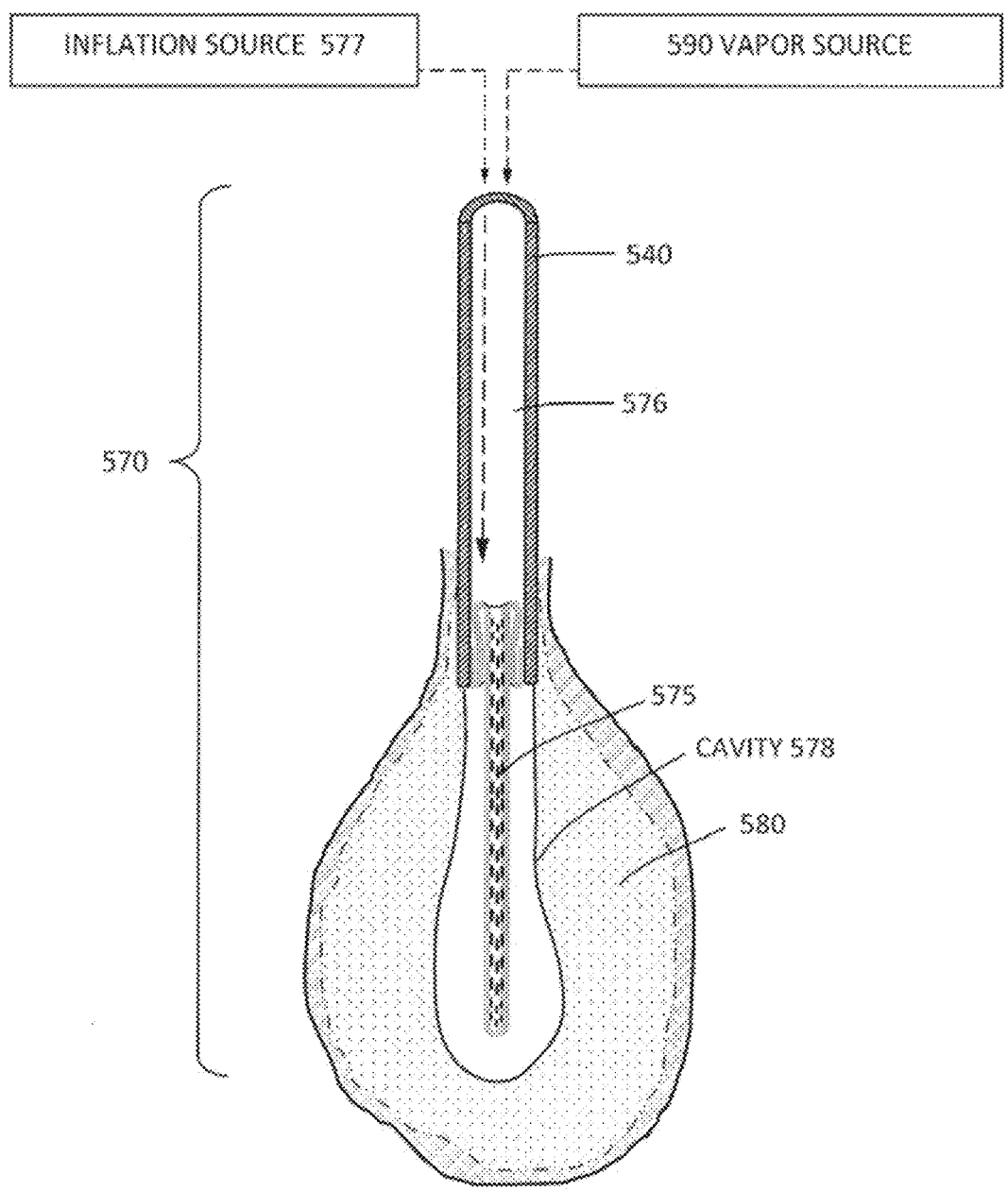
FIG. 11B is a view of the structure of FIG. 11A depicting an initial step of a method of expanding the thin-wall structure in a body cavity.
Figure 11C:
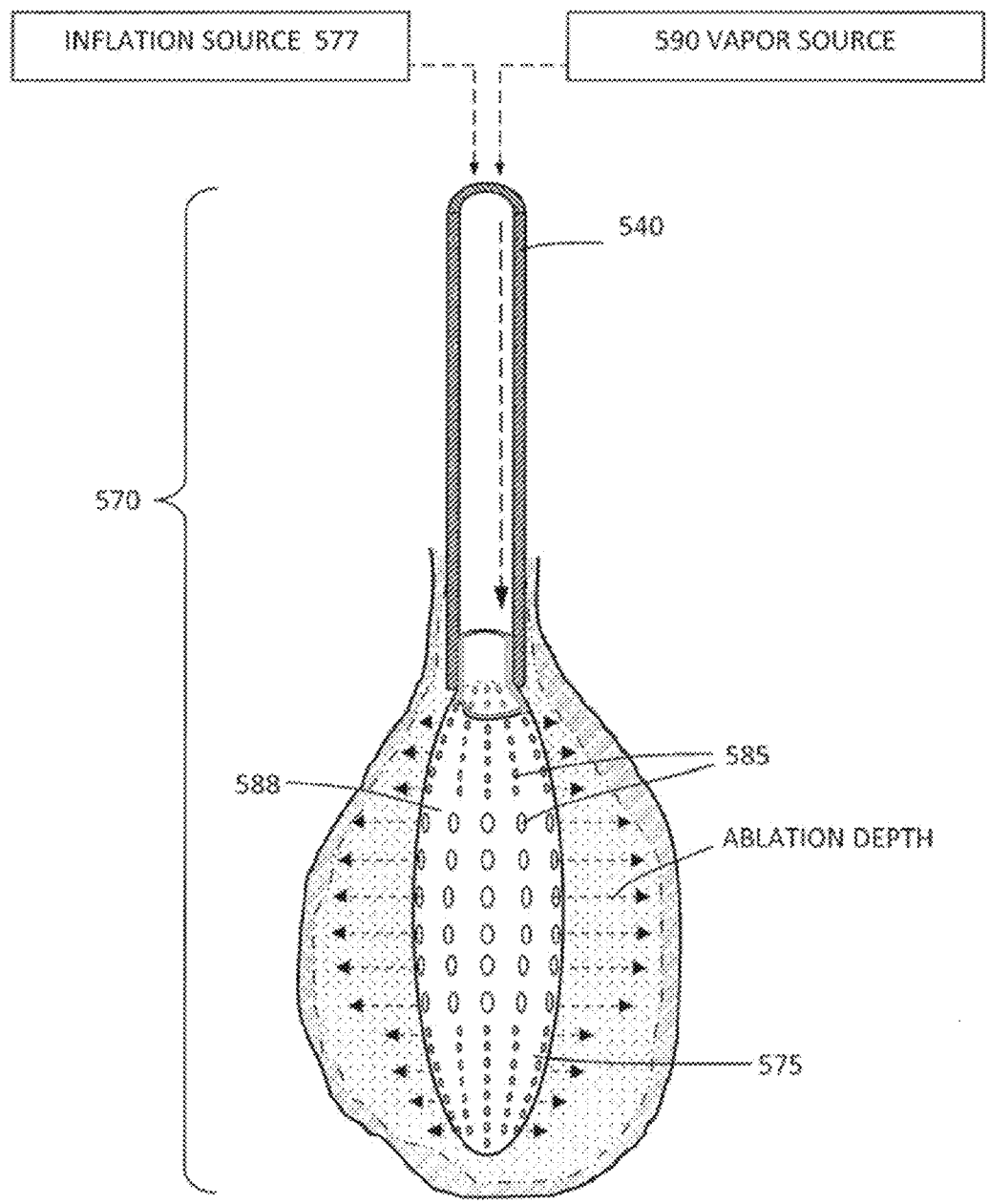
FIG. 11C is a sectional view of a structure of FIG. 11B in a deployed, expanded configuration depicting the step of delivering vapor into tissue surrounding the body cavity.

Now turning to FIGS. 11A-11C, a working end that operates similarly to that of FIG. 2 is shown. This embodiment comprises an extension member or other device 540 that can be positioned within a body region as shown in FIG. 11A. The device 540 includes a working end 570 that carries an evertable expansion structure or balloon 575 in interior bore 576. The expansion structure or balloon 575 is everted from within the device into the body region to apply energy to target tissue in the region as described below. By employing via everting, the structure 575 can fill or conform to a desired area within target region. In variations of the device, an everting balloon 575 can be fully positioned within the device 540 prior to everting. Alternatively, the everting balloon 575 can partially extend from an opening in the device 540 and then everted. FIGS. 11B-11C illustrate the balloon 575 being everted by application of fluid generated pressure from a first fluid source 577 (which can be any low pressure gas in a syringe) within a body cavity 578, for example, a cavity in gall bladder 580. However, additional variations of devices within this disclosure can employ any number of means to evert the balloon 575 from the device 540.

The region containing the target tissue includes any space, cavity, passage, opening, lumen or potential space in a body such as a sinus, airway, blood vessel, uterus, joint capsule, GI tract lumen or respiratory tract lumen. As can be seen in FIG. 11C, the expandable structure 575 can include a plurality of different dimension vapor outlets 585, for locally controlling the ejection pressure of a volume of ejected condensable vapor, which in turn can control the depth and extent of the vapor-tissue interaction and the corresponding depth of ablation. In embodiments described further below, the energy-emitting wall or surface 588 of the expandable structure can early RF electrodes for applying additional energy to tissue. Light energy emitters or microwave emitters also can be carried by the expandable structure. A vapor flow from source 590 or from any vapor generator source described above can flow high quality vapor from the vapor ports 585 in the wall or surface 588. The vapor outlets can be dimensioned from about 0.001" in diameter to about 0.05" and also can be allowed to be altered in diameter under selected pressures and flow rates. The modulus of a polymer wall 588 also can be selected to control vapor flows through the wall In general, a method of the invention as in FIG. 11C for treating a body cavity or luminal tissue comprises (a) everting and/or unfurling a thin-wall structure into the body cavity or lumen, and (b) applying at least 25 W, 50 W, 75 W, 100 W, 125 W and 150 W from an energy-emitter surface of the structure to the tissue, for example, the endometrium for ablation thereof in a global endometrial ablation procedure. In one embodiment, the method applies energy that is provided by a condensable vapor undergoing a phase change. In one embodiment, the method delivers a condensable vapor that provides energy of at least 250 cal/gm, 300 cal/gm, 350 cal/gm, 400 cal/gm and 450 cal/gm. Also, the method can apply energy provided by at least one of a phase change energy release, light energy, RF energy and microwave energy.

Figure 12A:
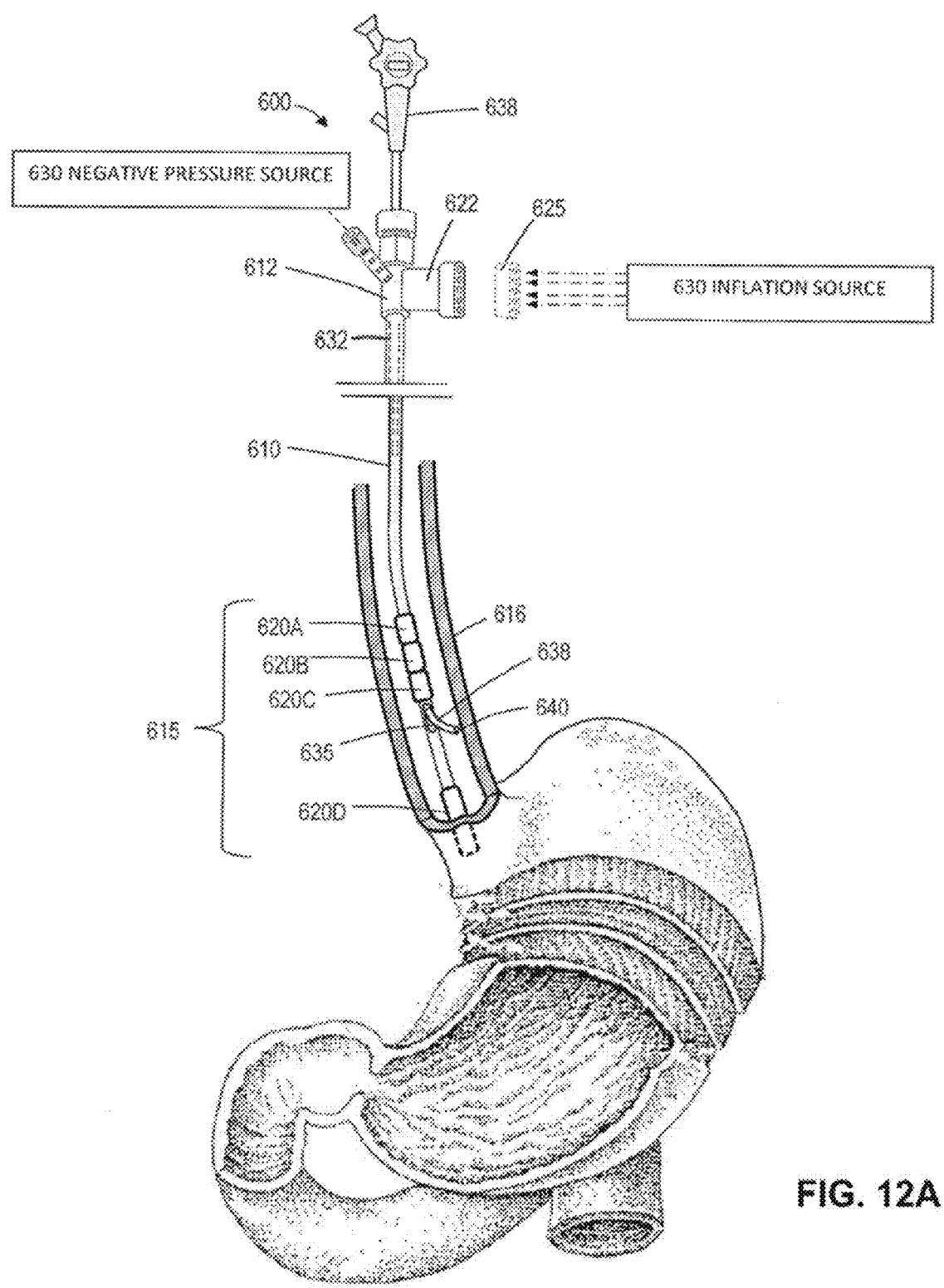
FIG. 12A is a schematic view of the handle and working end of vapor delivery tool for treating an esophageal disorder such as Barrett's esophagus.
Figure 12B:
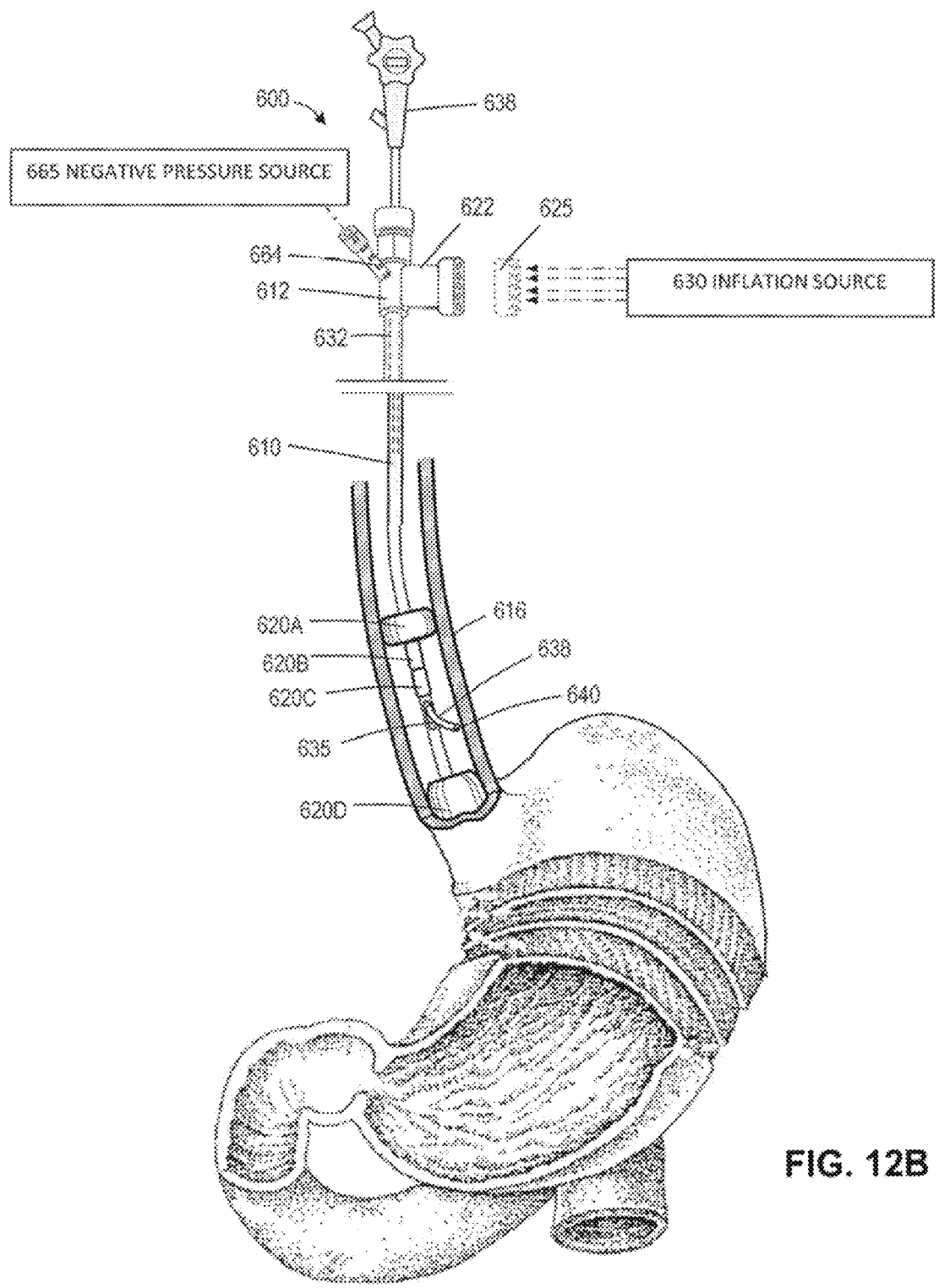
FIG. 12B is another view of the vapor delivery tool of FIG. 12A illustrating an initial step of a method of the invention comprising expanding proximal and distal occlusion balloons to define a treatment site between the balloons.
Figure 12C:
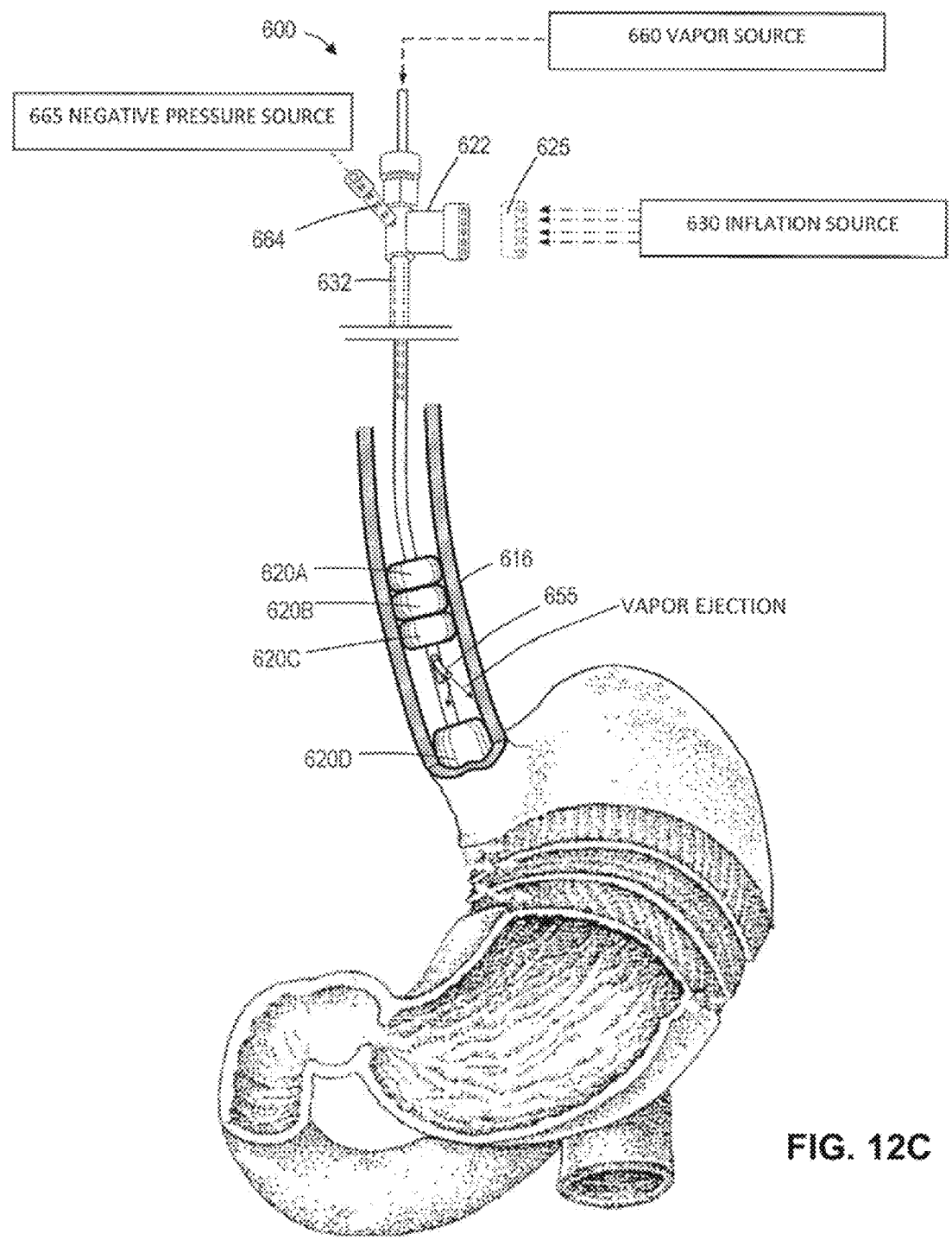
FIG. 12C is view similar to that of FIG. 12B illustrating a subsequent step of expanding one or more additional occlusion balloons to further circumscribe the targeted treatment site and the step of delivering vapor to ablate the esophageal lumen.

FIGS. 12A-12C depict another embodiment of vapor delivery system 600 that is configured for treating esophageal disorders, such as Barrett's esophagus, dysplasia, esophageal varices, tumors and the like. The objective of a treatment of an esophageal disorder is to ablate a thin layer of the lining of the esophagus, for example, from about 0.1 mm to 1.0 mm in depth. Barrett's esophagus is a severe complication of chronic gastroesophageal reflux disease (GERD) and seems to be a precursor to adenocarcinoma of the esophagus. The incidence of adenocarcinoma of the esophagus due to Barrett's esophagus and GERD is on the rise. In one method of the invention, vapor delivery can be used to ablate a thin surface layer including abnormal cells to prevent the progression of Barrett's esophagus.

The elongated catheter or extension member 610 has a first end or handle end 612 that is coupled to extension member 610 that extends to working end 615. The extension member 610 has a diameter and length suitable for either a nasal or oral introduction into the esophagus 616. The working end 615 of the extension member is configured with a plurality of expandable structures such as temperature resistant occlusion balloons 620A, 620B, 620C and 620D. In one embodiment, the balloons can be complaint silicone. In other embodiment, the balloons can be non-compliant thin film structures. The handle end 612 includes a manifold 622 that couples to multiple lumens to a connector 625 that allows for each balloon 620A, 620B, 620C and 620D to be expanded independently, for example, with a gas or liquid inflation source indicated at 630. The inflation source 630 can be a plurality of syringes, or a controller can be provided to automatically pump a fluid to selected balloons. The number of balloons carried by extension member 610 can range from 2 to 10 or more. As can be understood in FIGS. 12A-12C, the extension member 610 has independent lumens that communicate with interior chambers of balloons 620A, 620B, 620C and 620D.

Still referring to FIG. 12A, the handle and extension member 610 have a passageway 632 therein that extends to an opening 635 or window to allow a flexible endoscope 638 to view the lining of the esophagus. In one method, a viewing means 640 comprises a CCD at the end of endoscope 638 that can be used to view an esophageal disorder such as Barrett's esophagus in the lower esophagus as depicted in FIG. 12A. The assembly of the endoscope 638 and extension member 610 can be rotated and translated axially, as well as by articulation of the endoscope's distal end. Following the step of viewing the esophagus, the distal balloon 620D can be expanded as shown in FIG. 12B. In one example, the distal balloon 620D is expanded just distal to esophageal tissue targeted for ablative treatment with a condensable vapor. Next, the proximal balloon 620A can be expanded as also shown in FIG. 12B. Thereafter, the targeted treatment area of the esophageal lining can be viewed and additional occlusion balloons 620B and 620C can be expanded to reduce the targeted treatment area. It should be appreciated that the use of occlusion balloons 620A-620D are configured to control the axial length of a vapor ablation treatment, with the thin layer ablation occurring in 360° around the esophageal lumen. In another embodiment, the plurality of expandable members can include balloons that expand to engage only a radial portion of the esophageal lumen for example 90°, 180° or 270° of the lumen. By this means of utilizing occlusion balloons of a particular shape or shapes, a targeted treatment zone of any axial and radial dimension can be created. One advantage of energy delivery from a phase change is that the ablation will be uniform over the tissue surface that is not contacted by the balloon structures.

FIG. 12C illustrates the vapor delivery step of the method, wherein a high temperature water vapor is introduced through the extension member 610 and into the esophageal lumen to release energy as the vapor condenses. In FIG. 12C, the vapor is introduced through an elongated catheter 650 that is configured with a distal end 655 that is extendable slightly outside port 635 in the extension member 610. A vapor source 660, such as the vapor generator of FIG. 9 is coupled to the handle end 612 of the catheter. The catheter distal end 655 can have a recirculating vapor flow system as disclosed in commonly invented and co-pending application Ser. No. 12/167,155 filed Jul. 2, 2008. In another embodiment, a vapor source 660 can be coupled directly to a port and lumen 664 at the handle end 612 of extension member 610 to deliver vapor directly through passageway 632 and outwardly from port 635 to treat tissue. In another embodiment, as dedicated lumen in extension member 610 can be provided to allow contemporaneous vapor delivery and use of the viewing means 640 described previously.

The method can include the delivery of vapor for less than 30 seconds, less than 20 seconds, less than 10 seconds or less than 5 seconds to accomplish the ablation. The vapor quality as described above can be greater than 70%, 80% or 90% and can uniformly ablate the surface of the esophageal lining to a depth of up to 1.0 mm.

In another optional aspect of the invention also shown in FIGS. 12A-12C, the extension member 610 can include a lumen, for example the lumen indicated at 664, that can serve as a pressure relief passageway. Alternatively, a slight aspiration force can be applied to the lumen pressure relief lumen from negative pressure source 665.

Figure 13:
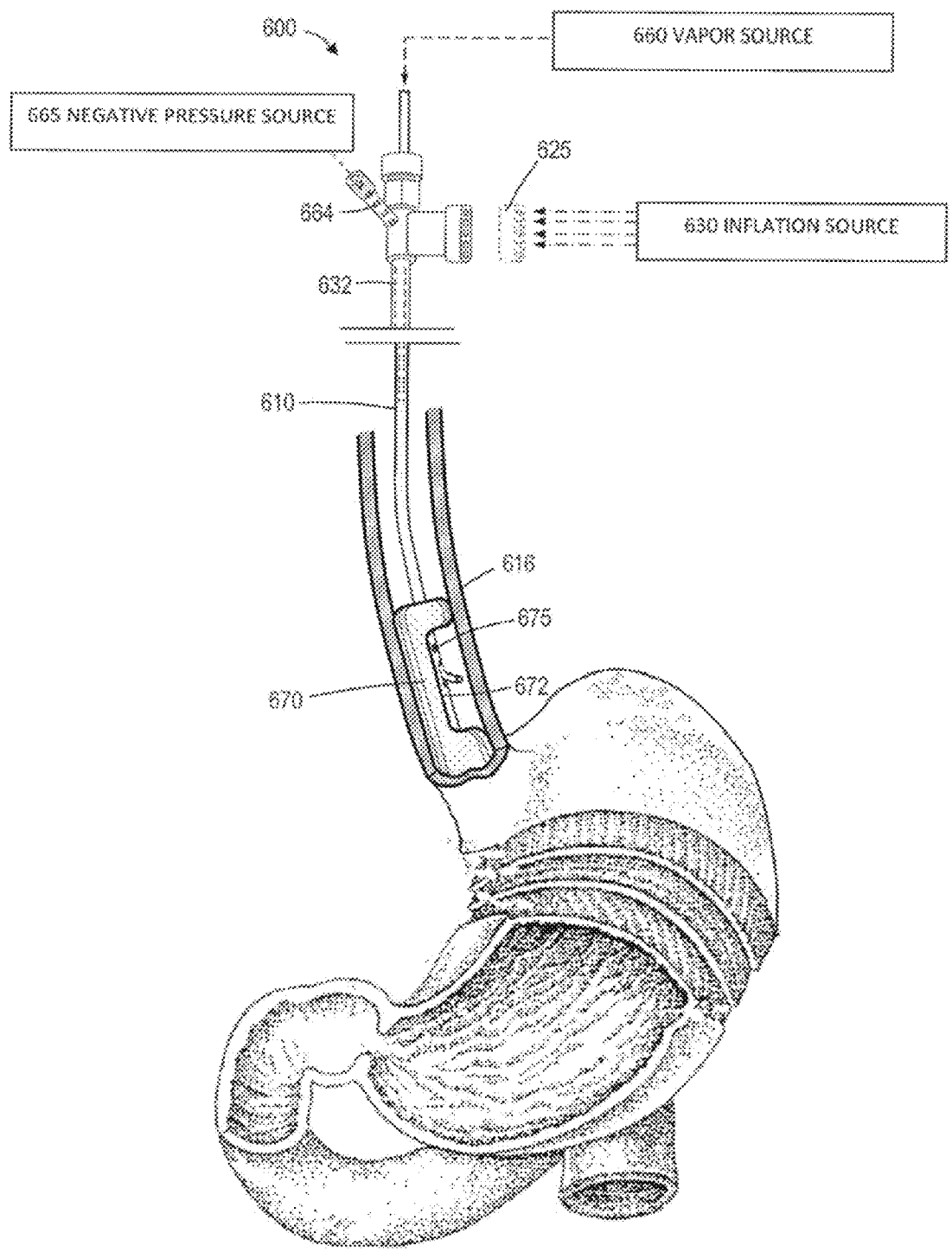
FIG. 13 is view similar to that of FIGS. 12A-12C illustrating an alternative embodiment and method for using a scalloped balloon for providing a less than 360° ablation the esophageal lumen.

FIG. 13 illustrates another aspect of the invention wherein a single balloon 670 can be configured with a scalloped portion 672 for ablating tissue along one side of the esophageal lumen without a 360 degree ablation of the esophageal lumen. In this illustration the expandable member or balloon 670 is radially positioned relative to at least one vapor outlet 675 to radially limit the condensable vapor from engaging the non-targeted region. As shown, the balloon 670 is radially adjacent to the vapor outlet 675 so that the non-targeted region of tissue is circumferentially adjacent to the targeted region of tissue. Although, the scalloped portion 672 allows radial spacing, alternative designs include one or more shaped balloons or balloons that deploy to a side of the port 675. FIG. 13 also depicts an endoscope 638 extended outward from port 635 to view the targeted treatment region as the balloon 670 is expanded. The balloon 670 can include internal constraining webs to maintain the desired shape. The vapor again can be delivered through a vapor delivery tool or through a dedicated lumen and vapor outlet 675 as described previously. In a commercialization method, a library of catheters can be provided that have balloons configured for a series of less-than-360° ablations of different lengths.

Figure 14:
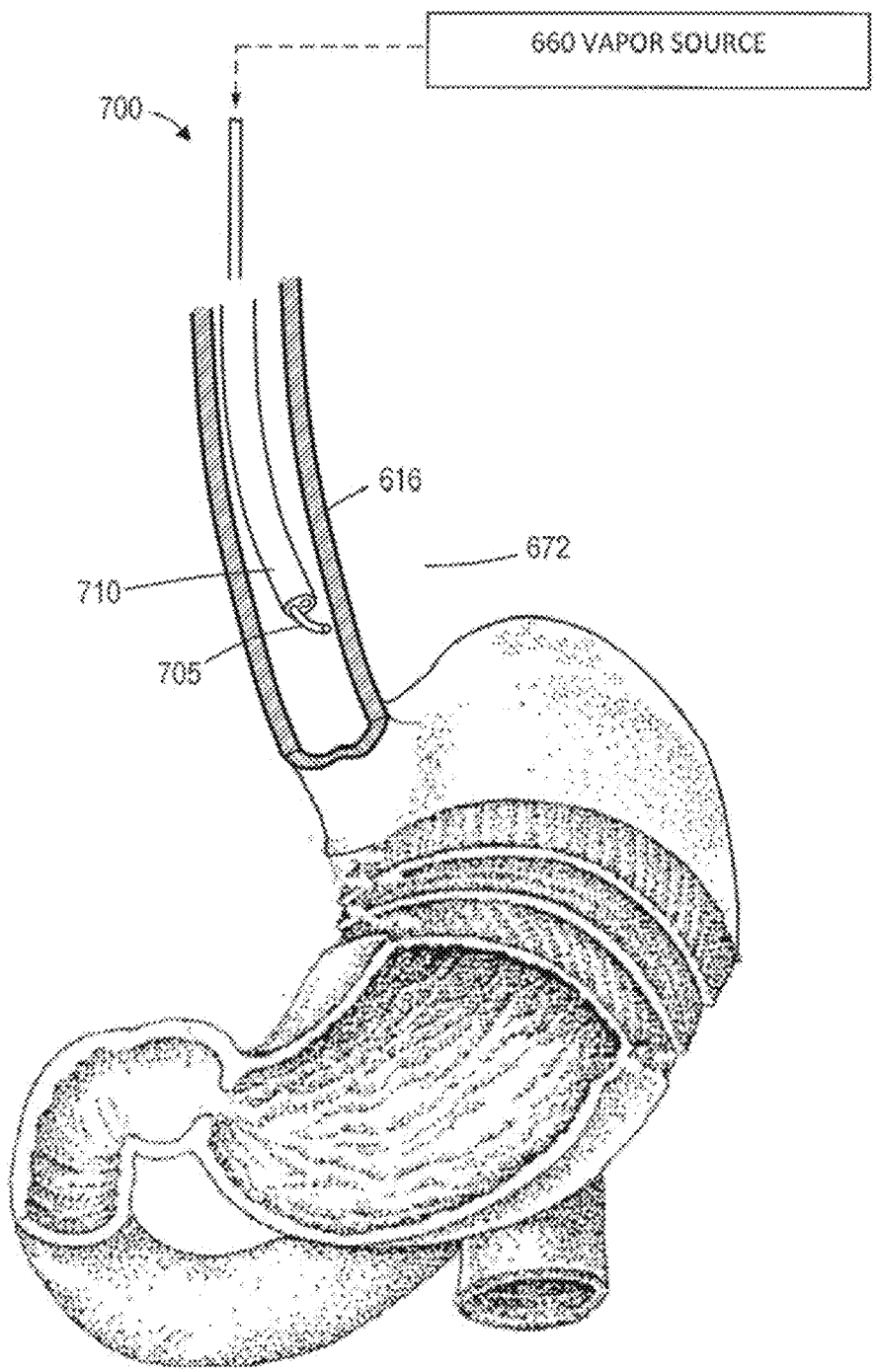
FIG. 14 depicts and alternative method for accomplishing a local ablation within the esophageal lumen utilizing an elongated vapor delivery tool introduced through a working channel of an endoscope.
Figure 15:
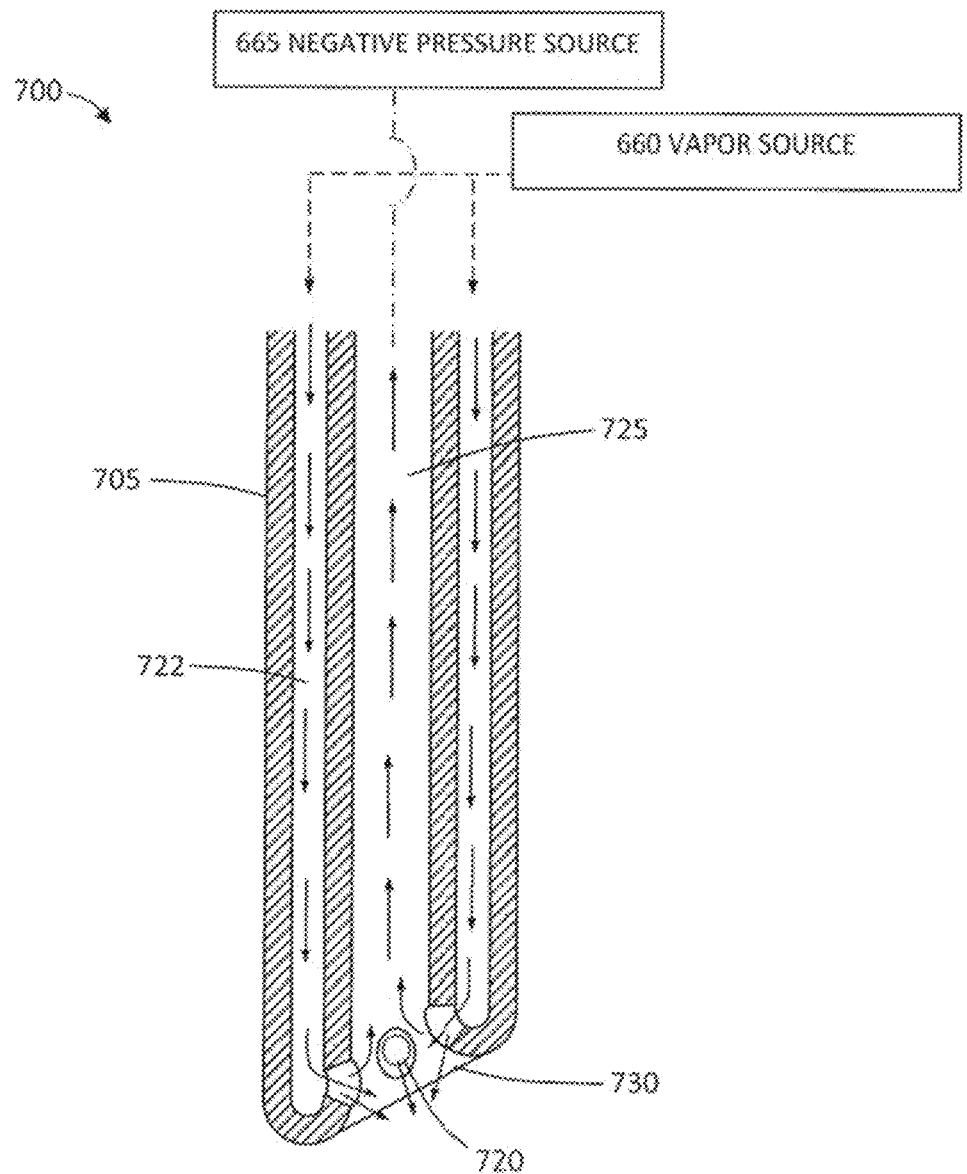
FIG. 15 is a sectional view of the working end of the vapor delivery tool of FIG. 14 showing vapor outlets that cooperates with an aspiration lumen for local control of vapor contact with tissue.

FIGS. 14-15 illustrate another embodiment and method of the invention that can be used for tumor ablation, varices, or Barrett's esophagus in which occlusion balloons are not used. An elongate vapor delivery catheter 700 is introduced along with viewing means to locally ablate tissue. In FIG. 14, catheter 700 having working end 705 is introduced through the working channel of gastroscope 710. Vapor is expelled from the working end 705 to ablate tissue under direct visualization. FIG. 15 depicts a cut-away view of one embodiment of working end in which vapor from source 660 is expelled from vapor outlets 720 in communication with interior annular vapor delivery lumen 722 to contact and ablate tissue. Contemporaneously, the negative pressure source 655 is coupled to central aspiration lumen 725 and is utilized to suction vapor flows back into the working end 705. The modulation of vapor inflow pressure and negative pressure in lumen 725 thus allows precise control of the vapor-tissue contact and ablation. In the embodiment of FIG. 15, the working end can be fabricated of a transparent heat-resistant plastic or glass to allow better visualization of the ablation. In the embodiment of FIG. 15, the distal tip 730 is angled, but it should be appreciated that the tip can be square cut or have any angle relative to the axis of the catheter. The method and apparatus for treating esophageal tissue depicted in FIGS. 14-15 can be use to treat small regions of tissue, or can be used in follow-up procedures after an ablation accomplished using the methods and systems of FIGS. 12A-13. In any of the above methods, a cooling media can be applied to the treated esophageal surface, which can limit the diffusion of heat in the tissue. Besides a cryogenic spray, any cooling liquid such as cold water or saline can be used.

Figure 16A:
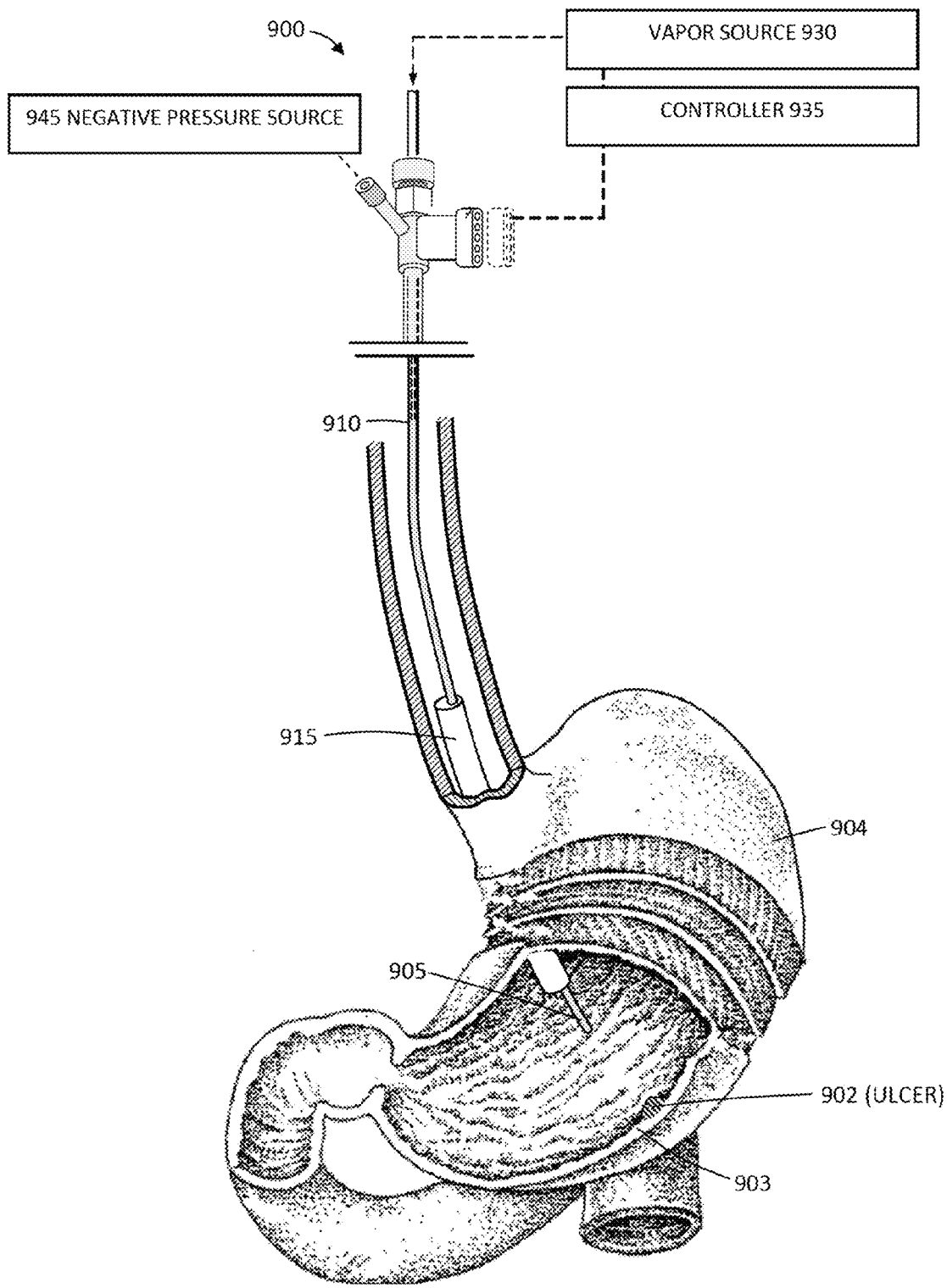
FIG. 16A is a view of an alternative vapor delivery tool configured for treating a wall of a body cavity, and depicts introducing the tool's working end into a stomach to treat a region of the wall of the body cavity.
Figure 16B:
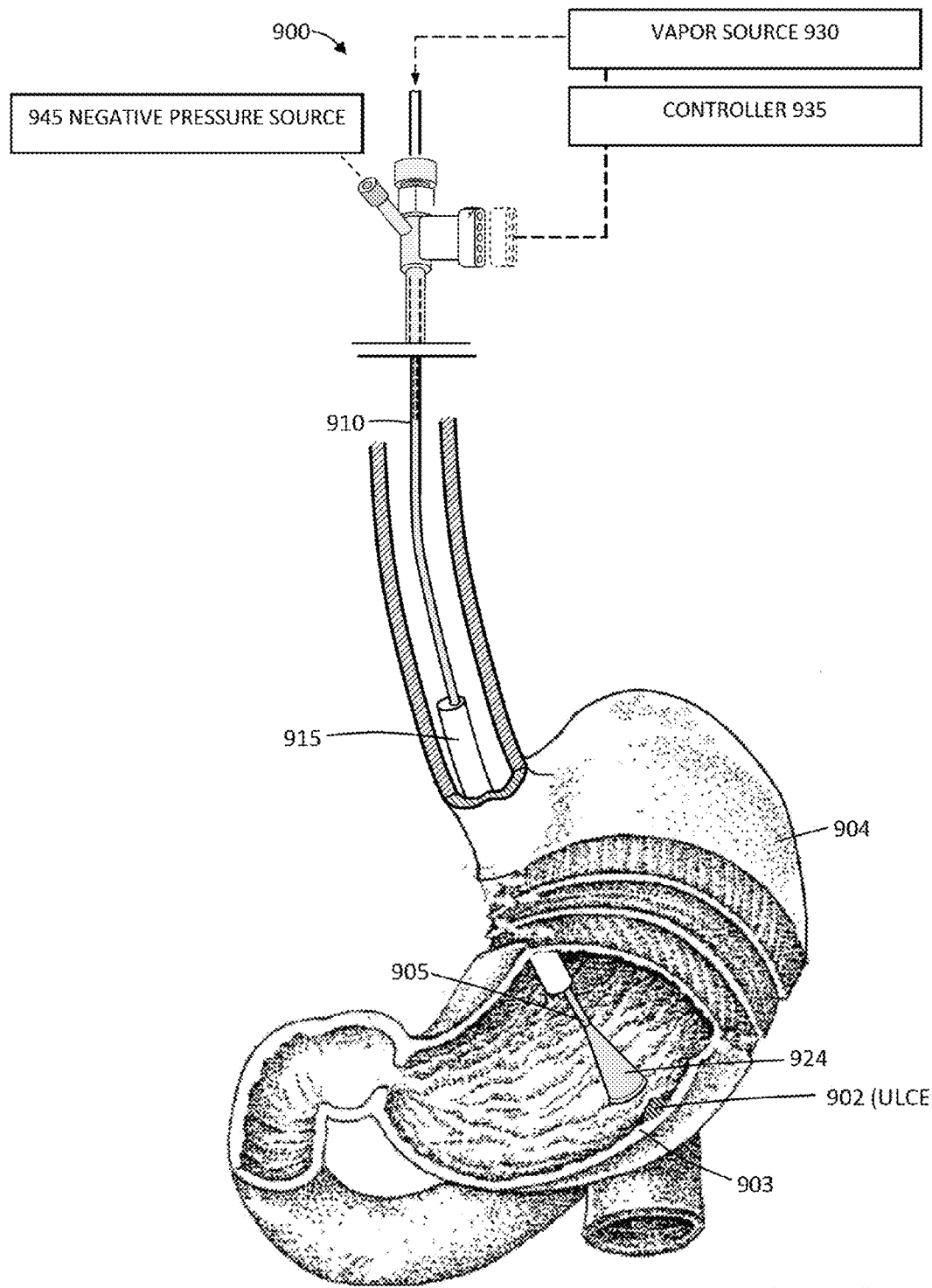
FIG. 16B is a schematic view similar to FIG. 16A illustrating the subsequent step of deploying an expandable portion of the catheter working end.

FIGS. 16A-16D depict another embodiment of vapor delivery system 900 that is configured for ablating a targeted tissue region 902 in a wall 903 of a body cavity, such as a bleeding ulcer in a patient's stomach 904. In FIG. 16A, it can be seen the working end 905 of a flexible vapor delivery catheter 910 is introduced through a working channel 912 of an endoscope 915. The physician can manipulate the endoscope 915 to the vicinity of the targeted tissue 902 in wall 903 of the patient's stomach 904. Alternatively, the delivery catheter 910 can be delivered directly without the use of an endoscope but through direct steering or manipulation of the catheter 910. In FIG. 16B, it can be seen that the working end 905 can be actuated to open an expandable portion of the working end 905. In one embodiment, referring to FIG. 17, working end 905 comprises an outer sleeve 920 and an extendable inner sleeve 922 that has a foldable or collapsible-expandable portion 924 that can be bell-shaped to provide a concavity 925 to position over the targeted tissue. The expandable portion 924 can comprise a thin wall, temperature resistant polymer, such as PEEK or a suitable transparent polymer, that has a repose bell-shape. Alternatively, the expandable portion 924 can comprise a thin wall silicone material with a metal spring element embedded therein to provide the expanded shape depicted in FIGS. 16B-16C.

Figure 16C:
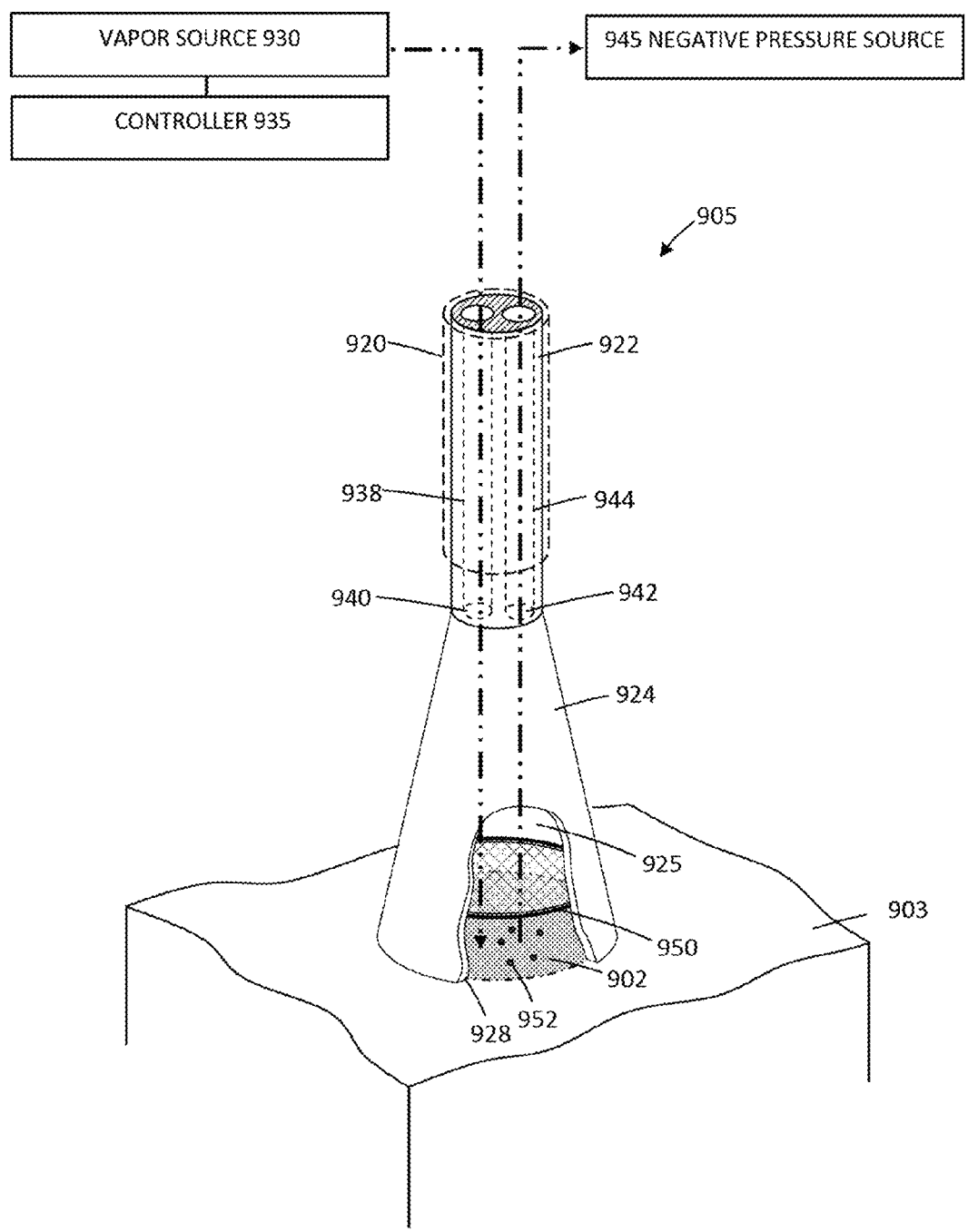
FIG. 16C is an enlarged cut-away view of the working end of FIG. 16B illustrating the subsequent step of engaging tissue with the expandable working end, delivering vapor media to the tissue interface, and circulating and filtering the vapor media to ablate the targeted tissue.
Figure 16D:
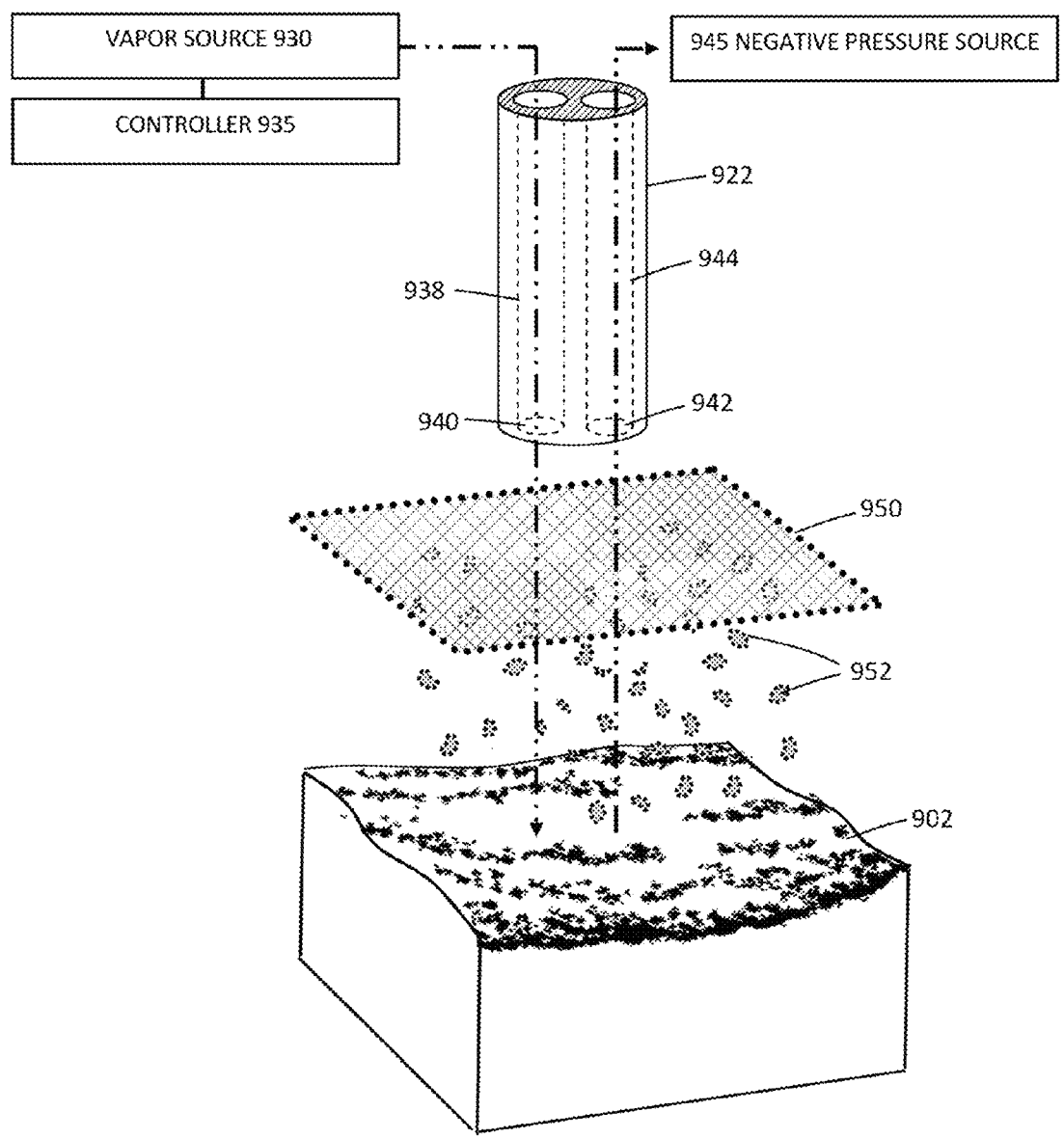
FIG. 16D is an enlarged schematic view of the working end of FIG. 16C illustrating the filter member capturing ablation detritus to insure the return flow channel is open.
Figure 17:
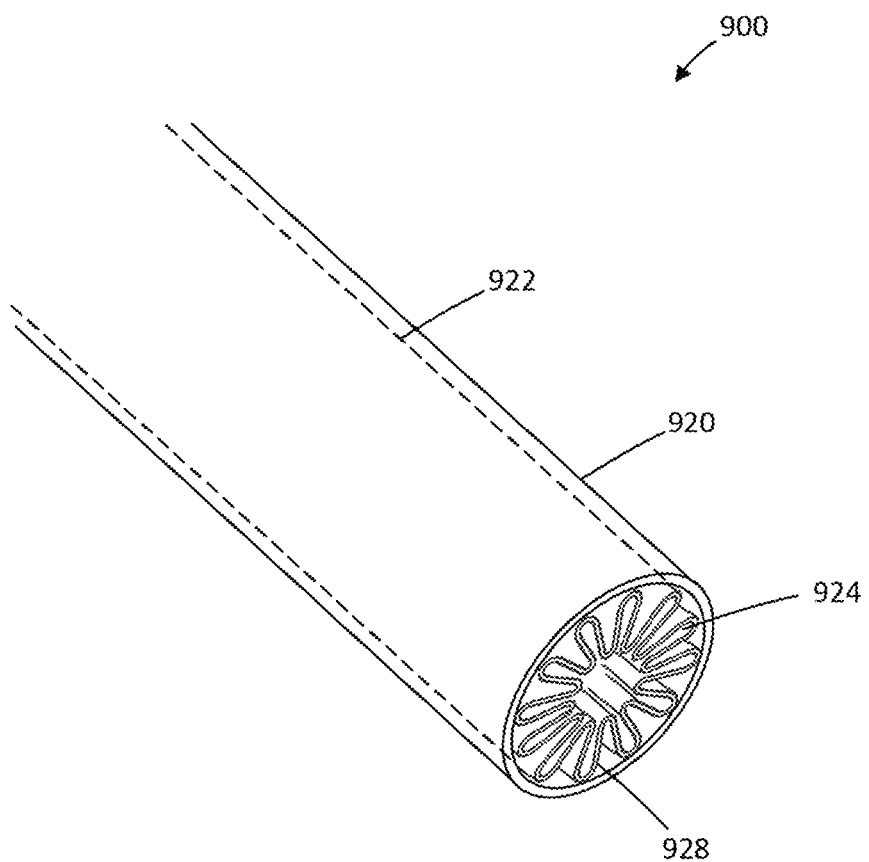
FIG. 17 is a perspective view of the working end of FIGS. 16A-16B illustrating an expandable portion of the folded working end retracted into an outer sleeve of the catheter.

FIG. 16C illustrates an enlarged schematic view of the expandable portion 924 of the working end 905 positioned over targeted tissue 902. The rim 928 of the expandable portion 924 can be pushed into contact with the wall 903. FIG. 16C further illustrates a vapor media comprising water vapor being introduced into the concavity 925 within expandable portion wherein the vapor undergoes a phase change and releases energy that ablates the targeted tissue. The vapor is delivered from vapor source 930 and controller 935 through an inflow channel 938 to a vapor outlet 940 in the working end, all of which is similar to previously described embodiments. In FIG. 16C, it can also be seen that the vapor media can circulate and condense in concavity 925 and thereafter flowable media (such as water droplets) can be extracted into extraction port 942 and return flow channel 944 of the catheter. The return flow of the flow media through port 942 and channel 944 can be assisted by negative pressure source 945 which is similar to previously described embodiments.

FIG. 16C further illustrates that the working end 905 is optionally configured with a filter member 950 that can comprise a collapsible flexible polymer screen or perforated thin film material bonded to the expandable portion 924. However, any type of material that provides a filtering effect can be used. In use, referring to FIGS. 16C-16D, it can be seen that the filter member 950 prevents ablation debris and tissue detritus 952 from moving from the targeted tissue surface toward the extraction port 942 which could clog the port 942 and limit or prevent the desired flow circulation through outflow channel 944. In some procedures to ablate tissue, there may be ablated tissue, coagulated blood or similar detritus 952 that will be captured by the filter member 950. It is desirable to provide a filter member 950 that has a surface area that is significantly greater than the cross-sectional area of extraction port 942 to insure that and detritus 952 captured by the filter member will not clog the entire surface of the filter. In one embodiment, the surface area of the filter member 950 is greater than the cross-sectional area of extraction port 942 by at least 200%, 400%, 600%, 800% or 1000%. It has been found that delivering a water vapor having a quality of 80% or 90% can provide a uniform ablation to a selected depth of 0.5 mm to 5 mm with a vapor delivery interval ranging between 5 seconds and 60 seconds. The method comprises delivering energy of at least 1 W, 5 W, 10 W, 25 W and 50 W into the targeted tissue.

In general, a method of the invention for ablating or coagulating tissue comprises introducing a device proximate to a targeted tissue in a body cavity such as a bleeding stomach ulcer and thermally treating the a targeted ulcer with vapor media introduced by the device. In this method, the thermal treatment is provided by a release of energy from a phase change of a vapor media, which can comprise water vapor. However, additional methods can include treatment of any body tissue using the methods and procedures described herein.

Figure 18:
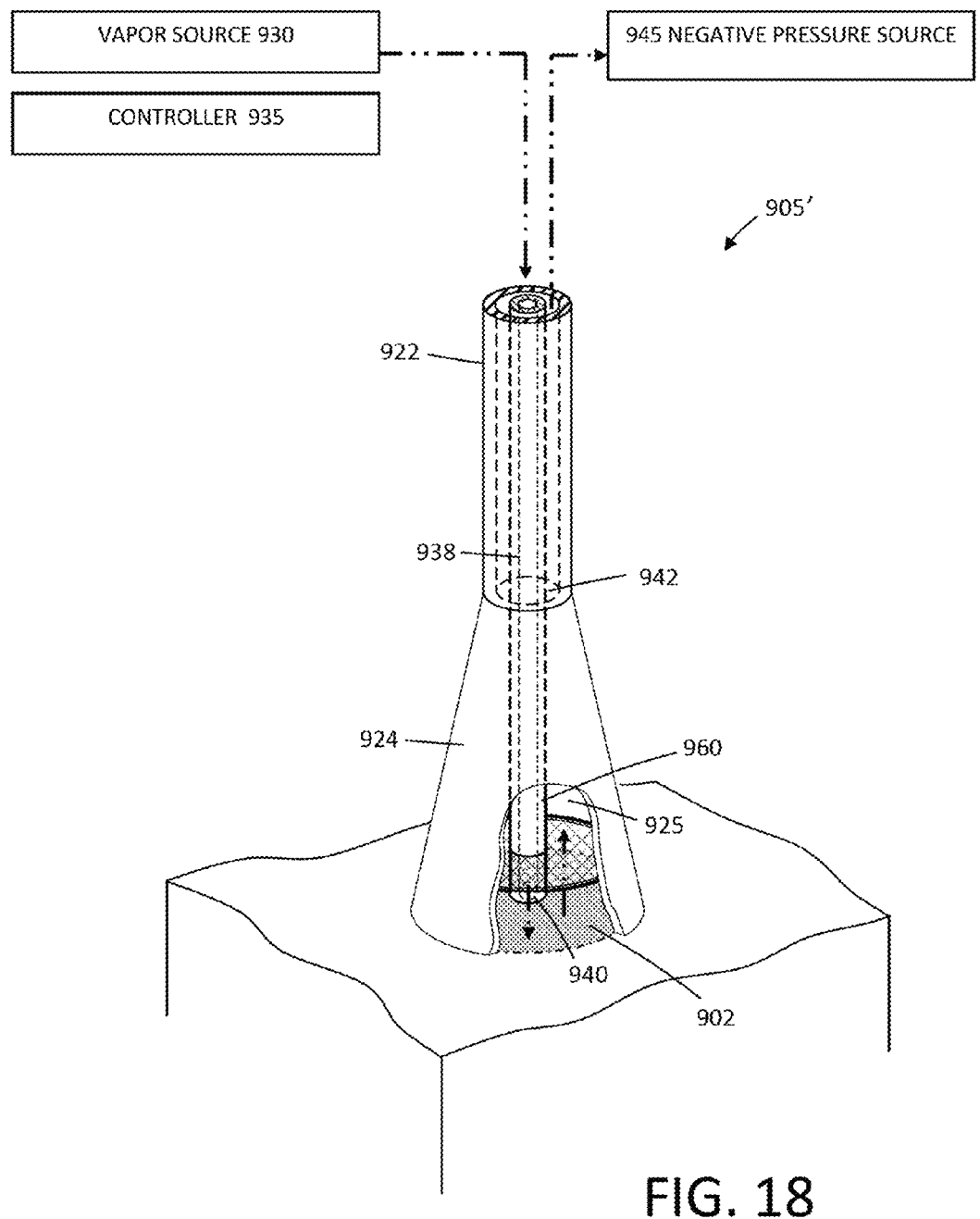
FIG. 18 is a schematic view of an alternative working end similar to that of FIGS. 16B-16D wherein the vapor outlet is distal of the filter member.

FIG. 18 depicts another embodiment of working end 905' that is similar to that of FIGS. 16B-16C. In the embodiment of FIG. 18, the vapor media inflow channel 938 is disposed in a sleeve 960 that extends through filter member 950 to thus provide the vapor outlet 940 in a location that is distal to the filter. Thus, the filter member 950 is positioned intermediate the vapor media outlet 940 and the extraction port 942. This configuration insures that vapor media is delivered distally of the filter member 950 which may be useful in situations wherein the filter 950 could become substantially covered with detritus, for example in a treatments that requires a lengthy vapor delivery intervals.

Figure 19:
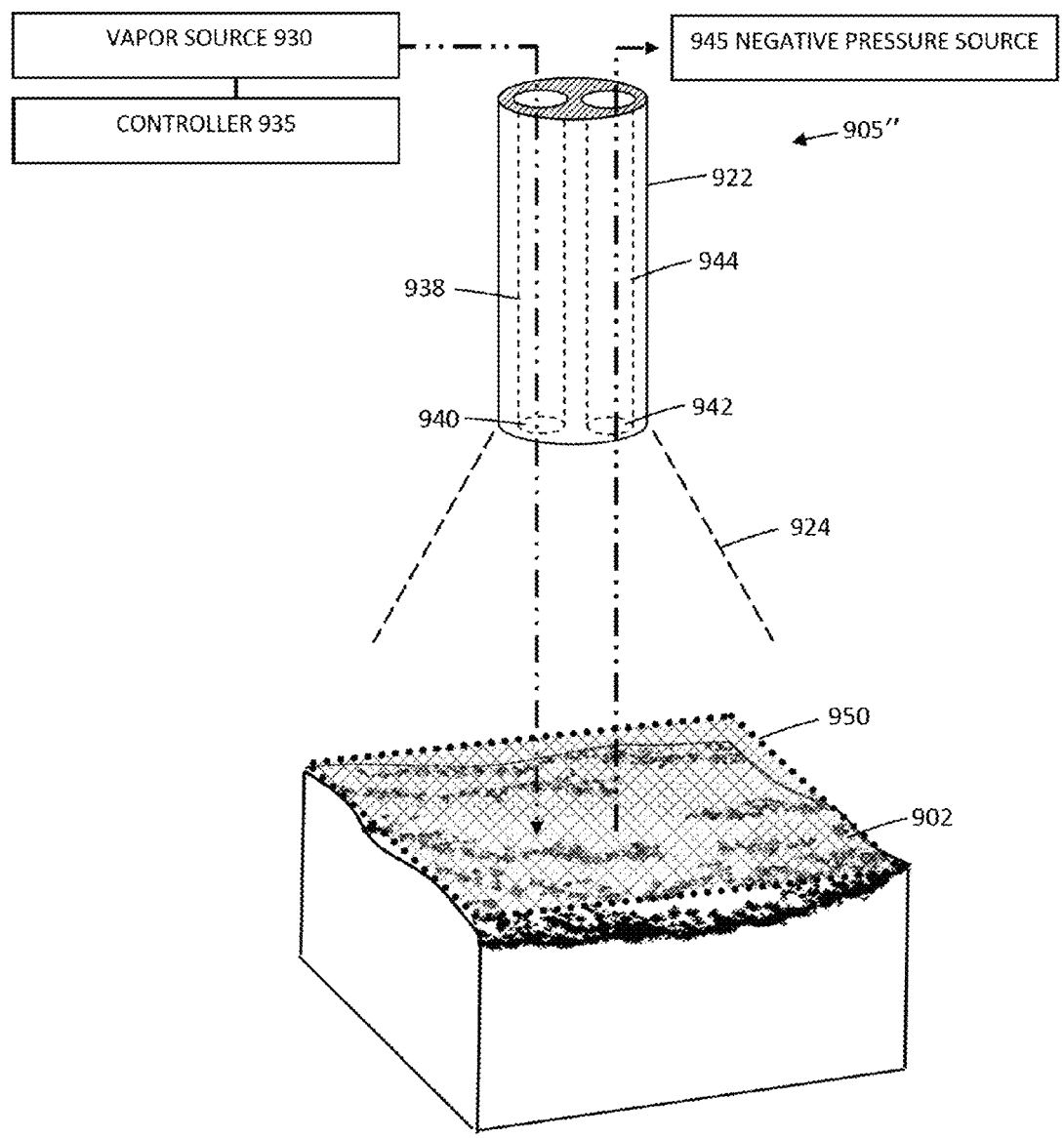
FIG. 19 is a schematic view of another working end similar to that of FIGS. 16B-16D and 18 wherein the filter member is provided at a surface of a working end to engage targeted tissue.

FIG. 19 schematically depicts another embodiment of working end 905" that is similar to that of FIGS. 16B-16C, and 18. In the embodiment of FIG. 19, the filter member 950 comprises at least a portion of an exterior surface of the working end, and the filter member 950 is thus configured to engage the targeted tissue surface 962 and confine any potential detritus to the tissue surface. In FIG. 19, the expandable portion 924 is indicated in phantom view, and it should be appreciated that the filter member can comprise any portion of a working end distal to the vapor inflow port 940 and extraction port 942.

Figure 20:
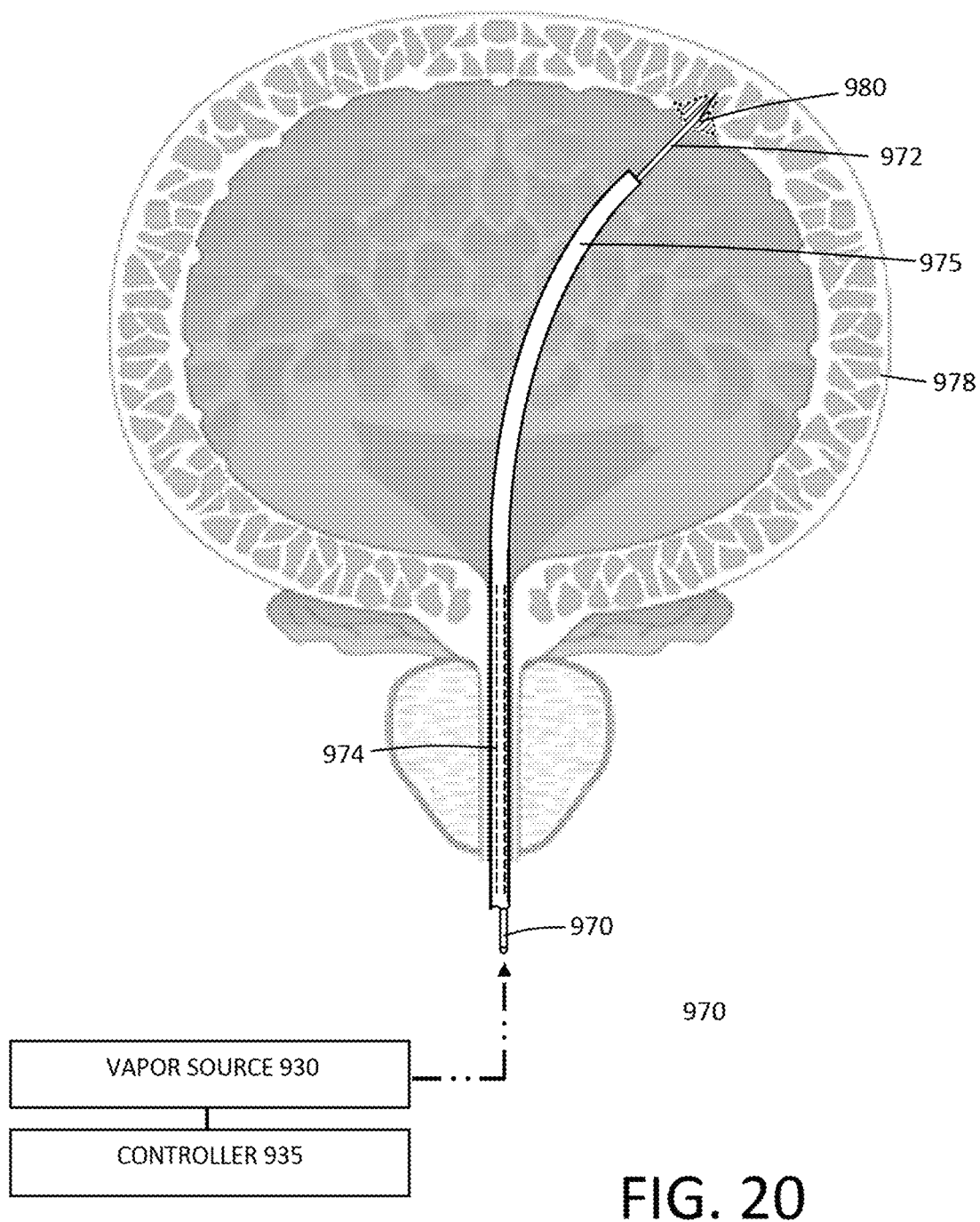
FIG. 20 is an illustration of an alternative vapor delivery tool configured for treating a tumor in a wall of a body cavity, such a bladder cancer tumor.

FIG. 20 illustrates another embodiment of a vapor delivery tool 970 that comprise flexible catheter or needle with a sharp working end 972 that is configured for penetrating into tissue and delivering vapor media into a subsurface region of targeted tissue. In one example, as shown in FIG. 20, the catheter and working end are introduced through the working channel 974 of an endoscope 975 disposed in a patient's bladder 978. In one embodiment, the catheter can comprise a PEEK sleeve with a sharpened tip. The sharp working end 972 is shown deployed in a bladder cancer tumor or lesion 980 wherein vapor delivery for 1 to 20 seconds can ablate the tumorous tissue. It should be appreciated the sharp working end 972 of FIG. 20 can be combined with the expandable portion 924 of FIG. 18 to provide both surface ablation effects and subsurface vapor energy delivery in the same procedure.

In general, a method corresponding to the invention for localized ablation of a targeted region of a wall of an organ, vessel, cavity or lumen comprises positioning a device working end proximate to a targeted tissue of the wall of a body organ, cavity, vessel or lumen, and introducing a flow media to the vicinity of the targeted tissue wherein a release of energy from a phase change of a water vapor portion of the flow media ablates the targeted tissue. The method can include delivering the flow media about a surface of the targeted tissue, injecting the flow media into subsurface portion of the targeted tissue, or both. In one method, the flow media is delivered in device working end is expandable and configures to contain the flow media. In another method, the working end is configured to contain and circulate the flow media between an outlet and an inlet port carried in the working end. In one method, a filter member is provided to prevent ablation detritus from entering the inlet port. By this means, the vapor media can provide a phase change energy release about or distal to the filter member to interface with, and ablate, the targeted tissue engaged by the working end. The method can target any tissue in a body cavity or lumen, as malignant tumors, benign tumors and growths, ulcers, polyps, fibroids, lesions, nodules, dysplasia or a bleeding surface of a tissue, organ, bone, body cavity or other body structure.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for treating an ulcer in a stomach tissue, the method comprising:

introducing a device proximate to a stomach ulcer;

generating a vapor with the device;

monitoring a vapor quality of the vapor by at least one sensor prior to applying the vapor to the stomach tissue;

positioning an expandable portion of the device having a concavity adjacent to the stomach tissue; and generating a flow of the vapor from a working end outlet of the device such that when the vapor contacts the stomach tissue within the concavity the vapor undergoes a phase change to thermally treat the ulcer in the stomach tissue;

wherein the concavity carries a flexible filter member, wherein the flexible filter member is configured to expand with the expandable portion to a greater diameter than an inlet, and wherein the inlet is in the working end outlet for allowing a return flow of the vapor.

2. The method of claim 1 wherein the thermal treatment is provided by a water vapor.

3. The method of claim 1 wherein the thermal treatment is provided by a release of energy from a phase change of a vapor media.

4. The method of claim 3 wherein the thermal treatment includes engaging tissue about the targeted ulcer within the concavity of the device.

5. The method of claim 4 wherein the vapor media is introduced into the concavity of the device.

6. The method of claim 4 further comprising aspirating media from the concavity of the device.

7. The method of claim 4 further comprising aspirating media through the flexible filter member.

8. The method of claim 4 further comprising utilizing a controller to control vapor media inflow and media outflow from the concavity.

9. The method of claim 4 further comprising expanding the working end outlet to form the concavity.

10. A method for locally treating a region of a wall of an organ, vessel, cavity or lumen the method comprising:
positioning a device proximate to a targeted tissue of the wall of a body organ, cavity, vessel or lumen;
positioning an expandable member of the device against the targeted tissue, where the expandable member includes a concavity;
producing a vapor flow media within the device;
monitoring a vapor quality of the vapor flow media by at least one sensor prior to applying the vapor flow media to the region of the wall;
introducing the vapor flow media within the concavity of the expandable member wherein a release of energy from a phase change of a water vapor portion of the flow media ablates the targeted tissue; and
continuing to monitor the vapor quality of the vapor flow by the at least one sensor;
wherein the concavity carries a filter member, wherein the filter member is configured to expand with the expandable member to a greater diameter than an inlet, and wherein the inlet is in a working end of the device for allowing a return flow of the vapor.

11. The method of claim 10 wherein the flow media is delivered about a surface of the targeted tissue.

12. The method of claim 10 wherein the flow media is injected into a subsurface portion of the targeted tissue.

13. The method of claim 10 wherein the flow media is delivered about a surface of the targeted tissue and injected into a subsurface portion of the targeted tissue.

14. The method of claim 10 wherein the flow media is delivered in the working end of the device that contains the flow media.

15. The method of claim 10 wherein the flow media is delivered in the working end of the device that circulates the flow media.

16. The method of claim 15 wherein the flow media circulates between an outlet and the inlet in the working end.

17. The method of claim 15 wherein the phase change energy release occurs about the filter member and tissue proximate the working end.

18. The method of claim 17 wherein the flow media circulation passes through the filter member intermediate the outlet and the inlet in the working end through the filter member.

19. The method of claim 17 wherein the filter member is configured to prevent ablation detritus from entering the inlet.

20. The method of claim 10 wherein the targeted tissue is selected from the group of malignant tumors, benign tissue, ulcers, polyps, fibroids, nodules and dysplasias.

21. A device for locally treating a region of a wall of an organ, vessel, cavity or lumen comprising:
a delivery tool configured to deliver a vapor flow from a working end outlet to an interface with a targeted tissue in the interior of a patient's body where the tool includes an expandable member having a concavity configured to be deployable from the delivery tool;
at least one sensor configured to monitor a vapor quality of the vapor flow prior to applying the vapor flow to the region of the wall;
an inlet in the working end for allowing a return flow of the vapor flow; and
a flexible filter member carried within the concavity of the expandable member such that it can expand with the expandable member to a greater diameter than the inlet and configured to prevent ablation detritus from entering the inlet.

22. The device of claim 21 wherein the filter member comprises at least in part a working end surface configured to substantially contact the targeted tissue.

23. The device of claim 21 wherein the filter member is positioned intermediate the outlet and the inlet.

24. The device of claim 21 wherein the filter member has a surface area that is greater than the cross section of the inlet by at least 200%.

25. A method for contained treatment of a region of tissue, the method comprising:
positioning a flow media device proximate to the region of tissue where the flow media device is configured to deliver a flow media through a delivery port, where the flow media releases an amount of energy to the region of tissue from a phase change of the flow media;
controlling a vapor quality of the flow media prior to delivering the vapor flow media from the flow media device;
deploying at least one expandable structure from a distal portion of the flow media device to define a treatment cavity;
fluidly separating the region of tissue from adjacent tissue by contacting the at least one expandable structure against the region of tissue; and
delivering the vapor flow media into the treatment cavity such that the vapor flow media is contained within the treatment cavity and engages the region of tissue to ablate the tissue;
wherein the at least one expandable structure has a concavity, wherein the concavity carries a filter, wherein the filter is configured to expand with the at least one expandable structure to a greater diameter than an inlet, and wherein the inlet is in a working end of the device for allowing a return flow of the vapor.

26. The method of claim 25 further comprising applying an aspiration source through an aspiration port to the treatment cavity to aspirate the flow media.

27. The method of claim 26 further comprising positioning the filter within the cavity such that the aspirated flow media is filtered prior to aspiration.

28. The method of claim 27 where positing the filter comprises placing the filter adjacent to the region of tissue such that the filter separates the region of tissue from the delivery port and aspiration port.

29. The method of claim 28 where the filter is placed in contact with the region of tissue.

30. The method of claim 27 where positing the filter comprises placing the filter adjacent to the region of tissue and proximal of the delivery port such that the filter separates the region of tissue from the aspiration port and so that the delivery port delivers the flow media directly to the region of tissue.

31. The method of claim 25 wherein the flow media is delivered to a surface of the region of tissue.

32. The method of claim 25 wherein the flow media is injected into a subsurface portion of the region of tissue.

33. The method of claim 25 wherein the flow media is delivered to a surface of the region of tissue and injected into a subsurface portion of the targeted tissue.

34. The method of claim 25 where delivering the flow media into the cavity comprises circulating the flow media within the cavity.

* * * * *